US011547708B2

(12) United States Patent
Ou et al.

(10) Patent No.: US 11,547,708 B2
(45) Date of Patent: Jan. 10, 2023

(54) COMPOSITIONS AND METHODS TO PROTECT MAMMALIAN TISSUE AGAINST COLD AND OTHER METABOLIC STRESSES

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Jingxing Ou, Bethesda, MD (US); Wei Li, Potomac, MD (US); Kiyoharu Josh Miyagishima, Laurel, MD (US)

(73) Assignee: THE USA, AS REPRESENTED BY THE SECRETARY, DHHS, Bethesda, MD (US)

( * ) Notice: Subject to any disclaimer, the term of this patent is extended or adjusted under 35 U.S.C. 154(b) by 26 days.

(21) Appl. No.: 16/636,945

(22) PCT Filed: Aug. 20, 2018

(86) PCT No.: PCT/US2018/047064
§ 371 (c)(1),
(2) Date: Feb. 6, 2020

(87) PCT Pub. No.: WO2019/040359
PCT Pub. Date: Feb. 28, 2019

(65) Prior Publication Data
US 2020/0368230 A1 Nov. 26, 2020

Related U.S. Application Data

(60) Provisional application No. 62/547,945, filed on Aug. 21, 2017.

(51) Int. Cl.
*A61K 31/4985* (2006.01)
*A61K 31/336* (2006.01)
*A61K 31/34* (2006.01)
*A61K 38/08* (2019.01)
*A61K 45/06* (2006.01)

(52) U.S. Cl.
CPC ........ *A61K 31/4985* (2013.01); *A61K 31/336* (2013.01); *A61K 31/34* (2013.01); *A61K 38/08* (2013.01); *A61K 45/06* (2013.01)

(58) Field of Classification Search
CPC .. A61K 31/137; A61K 31/197; A61K 31/336; A61K 31/34; A61K 31/5395; A61K 31/4985; A61K 38/08; A61K 38/55; A61P 43/00

See application file for complete search history.

(56) References Cited

U.S. PATENT DOCUMENTS

2004/0096813 A1* 5/2004 Baust ............... A01N 1/02
 435/2
2008/0269161 A1* 10/2008 Perry ............... A61K 31/64
 514/45

FOREIGN PATENT DOCUMENTS

| JP | 2012116823 A | * | 6/2012 |
| WO | 0002572 A1 | | 1/2000 |
| WO | 2013192388 A1 | | 12/2013 |
| WO | 2014041125 A1 | | 3/2014 |

OTHER PUBLICATIONS

English translation of JP 2012-116823, pp. 1-25 (Year: 2012).*
Yeh et al., J. Thorac. Cardiovas. Surg., vol. 104, pp. 659-665, publ. 1992 (Year: 1992).*
Ou et al., Cell, vol. 173, pp. 851-853, publ. 2018 (Year: 2018).*
International Preliminary Report on Patentability issued in Application No. PCT/US2018/047064, International Filing Date Aug. 20, 2018, Report dated Feb. 25, 2020, 9 pages.
Alexander Y. Petrenko et al., "Reversible mitochondrial uncoupling in the cold phase during liver preservation/reperfusion reduces oxidative injury in the rat model" Cryobiology, vol. 60, No. 3, Feb. 10, 2010, pp. 293-300.
Brandon M. Kenwood et al., "Identification of a novel mitochondrial uncoupler that does not depolarize the plasma membrane" Molecular Metabolism, vol. 3, No. 2, Apr. 1, 2014, pp. 114-123.
International Search Report issued in Application No. PCT/US2018/047064 dated Nov. 26, 2018; International Filing Date Aug. 20, 2018, 7 pages.
Kenwood et al., "Structure-Activity Relationships of Furazano[3,4-b]Pyrazines as Mitochondrial Uncouplers," Bioorganic& Medicinal Chemistry Letters, vol. 25, No. 21, Nov. 1, 2015; pp. 4858-4861, XP055414210.
Tanecia Mitchell et al., "The Mitochondria-Targeted Antioxident Mitoquinone Protects against Cold Storage Injury of Renal Tubular Cells and Rat Kidneys" The Journal of Pharmacology and Experimental Therapeutics, vol. 336, No. 3, Mar. 1, 2011, p. 682-692.
Willem J. Laursen et al., "Neuronal UCP1 expression suggests a mechanism for local thermogenesis during hibernation" PNAS, vol. 112, No. 5, Feb. 3, 2015, pp. 1607-1612.
Written Opinion issued in International Application No. PCT/US2018/047064 dated Nov. 26, 2018; International Filing Date Aug. 20, 2018, 11 pages.

* cited by examiner

*Primary Examiner* — Sarah Pihonak
(74) *Attorney, Agent, or Firm* — McBee Moore & Vanik IP, LLC

(57) ABSTRACT

A composition for preserving viability of cells, tissues, or organs at a low temperature is provided. The composition includes a mitochondrial uncoupling agent, at least one protease inhibitor, and a reducing agent. Methods to protect cells, tissues, or organs from exposure to cold and other metabolic stress are also provided.

11 Claims, 55 Drawing Sheets

FIG. 7G

TBB3_HUMAN|Q13509 SGAGNNWAKGHYTEGAE 95-111
TBB3_MOUSE|Q9ERD7 SGAGNNWAKGHYTEGAE 95-111
TBB3_RAT|Q4QRB4 SGAGNNWAKGHYTEGAE 95-111
I3MXL4_ICTTR|I3MXL4 SGAGNNWAKGHYTEGAE 95-111

TBB3_HUMAN|Q13509 EESEAQGPK 442-450
TBB3_MOUSE|Q9ERD7 EESEAQGPK 442-450
TBB3_RAT|Q4QRB4 EESEAQGPK 442-450
I3MXL4_ICTTR|I3MXL4 EESEAQGPK 442-450

COMPOSITIONS AND METHODS TO PROTECT MAMMALIAN TISSUE AGAINST COLD AND OTHER METABOLIC STRESSES

CROSS-REFERENCE TO RELATED APPLICATIONS

This application is a U.S. National Stage application of International Application No. PCT/US2018/047064 filed on Aug. 20, 2018 which claims priority to U.S. Provisional Application No. 62/547,945 filed on Aug. 21, 2017, both of which are hereby incorporated by reference in their entireties.

BACKGROUND OF THE INVENTION

Field of Invention

The present invention is directed to composition and methods enabling non-hibernating mammals to withstand severe cold conditions, and more specifically to compositions and methods to protect, e.g., cells, tissues and organs of non-hibernating mammals against cold and other metabolic stresses.

Brief Description of Related Art

Therapeutic hypothermia is a surgical management technique to protect brain injury or trauma from inflammation and free radicals during surgery, and is achieved by deliberate reduction of the core body temperature. Therapeutically induced hypothermia counteracts neuroexcitation in brain cells by stabilizing calcium and glutamate release, thereby reducing the degree of cell death. It also stabilizes the blood-brain barrier and suppresses the inflammatory process, reducing cerebral edema. As cerebral metabolism declines, the brain needs less oxygen.

Mild hypothermia is present when the core body temperature is 34-35° C., and moderate hypothermia is present when the core body temperature is 31-33° C. Although mild hypothermia and moderate hypothermia can be achieved in practice, many complications associated with them have been recognized, including, for example, fluid and electrolyte imbalances, arrhythmias, insulin resistance, shivering, and coagulation problems. It therefore has been postulated that severe therapeutic hypothermia around 4-5° C. would be more beneficial and preferred to mitigate the above adverse effects during the surgery. However, current approaches to induce severe therapeutic hypothermia in a patient may cause irreversible damage and increased complications.

Meanwhile, neural transplantation therapy to replace damaged neurons is a new and promising approach to the treatment of progressive neurodegenerative disorders, such as Parkinson's disease that affects patient's movement due to lack of dopamine. One of the most effective and well-advanced treatment has been the transplantation of new, undamaged cells to replenish those that are lost or dying. In this procedure, cells from the developing fetus membrane have been transplanted into the striatum of the patient, to a site where dopamine normally functions. While replacement of the damaged neurons has achieved notable success in clinic, it is still a challenge to maintain in vitro survival activity of isolated neural cells or tissue transplants at low temperature prior to transplantation.

Because warm ischemic conditions damage donor organs such as kidneys, they commonly undergo cold storage. However, prolonged cold storage has been shown to induce mild oxidative stress and related cellular damage. To this effect, antioxidants have been shown in rat, dog, and porcine kidneys to alleviate cold-induced oxidative injury. Therefore, as the standard cold storage solution used in organ preservation, so-called University of Wisconsin (UW) solution is enriched in antioxidant components. Nonetheless, even with UW solution or other physiological solutions, cold-induced disruption and degradation of microtubules still occur.

Therefore, there is a need for an improved composition and method for preserving organs, tissues or cells at a temperature of around 4-5° C. that is useful for both low-temperature therapeutic hypothermia and transplantation. The present invention is believed to be an answer to that need.

SUMMARY OF THE INVENTION

In one embodiment, the present invention is directed to a composition for preserving the viability of cells, tissues, or organs during exposure to a low temperature environment. The composition includes a mitochondrial uncoupling agent, at least one protease inhibitor, and a reducing agent.

In another embodiment, the invention is directed to a method for treating mammalian cells, tissues, or organs to withstand exposure to a low temperature environment during therapy, treatment, or a medical procedure, the method comprising the steps of providing mammalian cells, tissues, or organs to be exposed to a low temperature environment; providing a composition comprising a mitochondrial uncoupling agent, at least one protease inhibitor, and a reducing agent; and contacting the mammalian cells, tissues, or organs with the composition to enable the mammalian cells, tissues, or organs withstand exposure to a low temperature environment.

BRIEF DESCRIPTION OF THE DRAWINGS

The above and other aspects and features of the present disclosure will become more apparent in the following detailed description when taken in conjunction with reference to the accompanying drawings, in which:

FIGS. 7A to 7G depict bioinformatics analyses on GS and human iPSC-neurons;

Figure 13A:
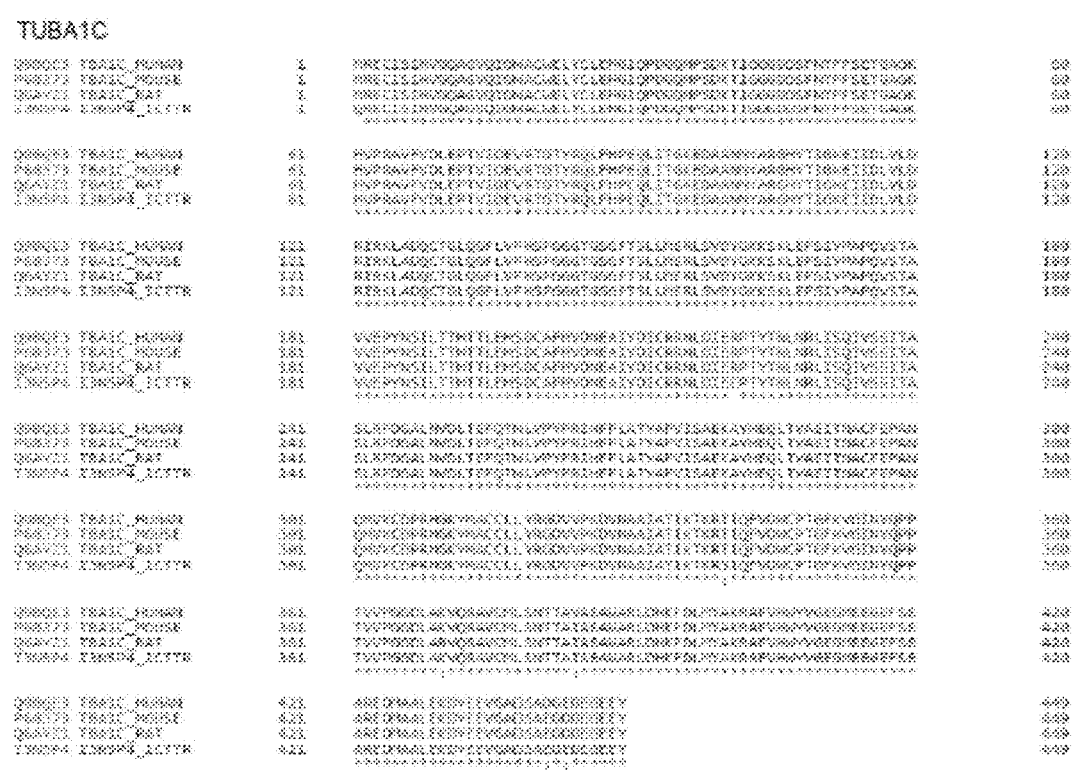
Figure 13B:
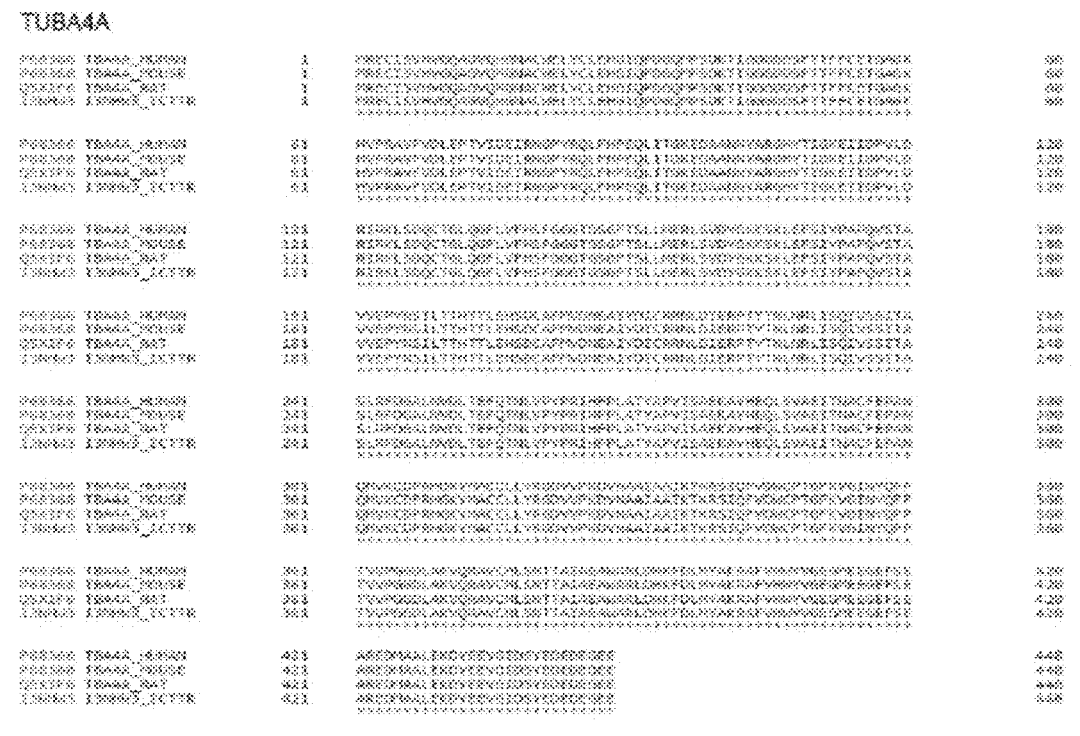
Figure 13C:
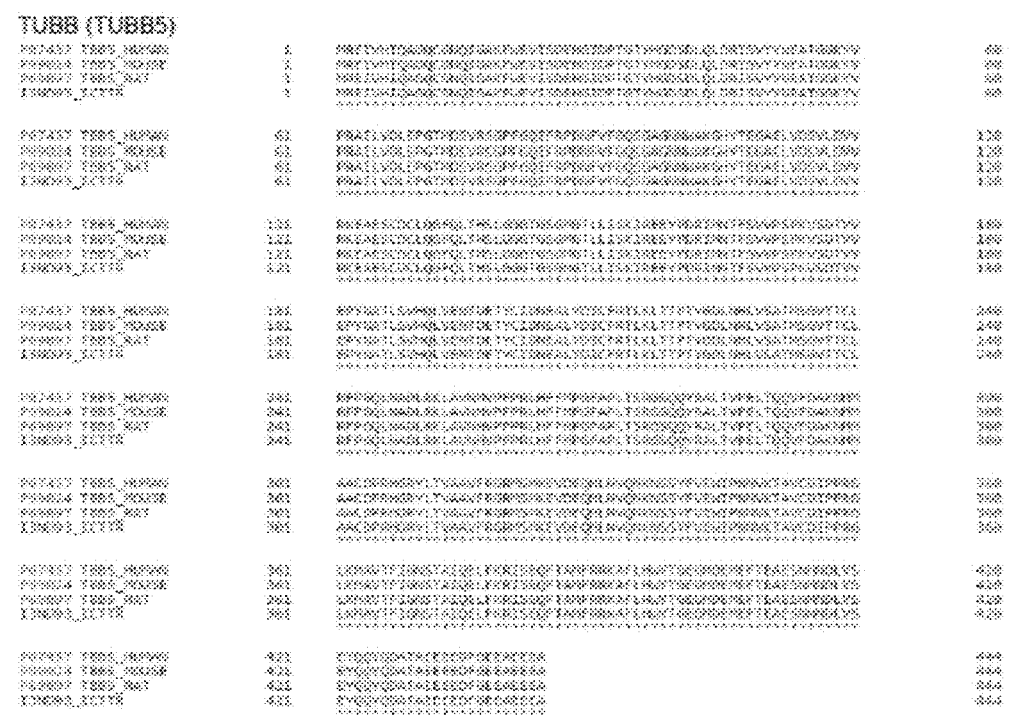
Figure 13D:
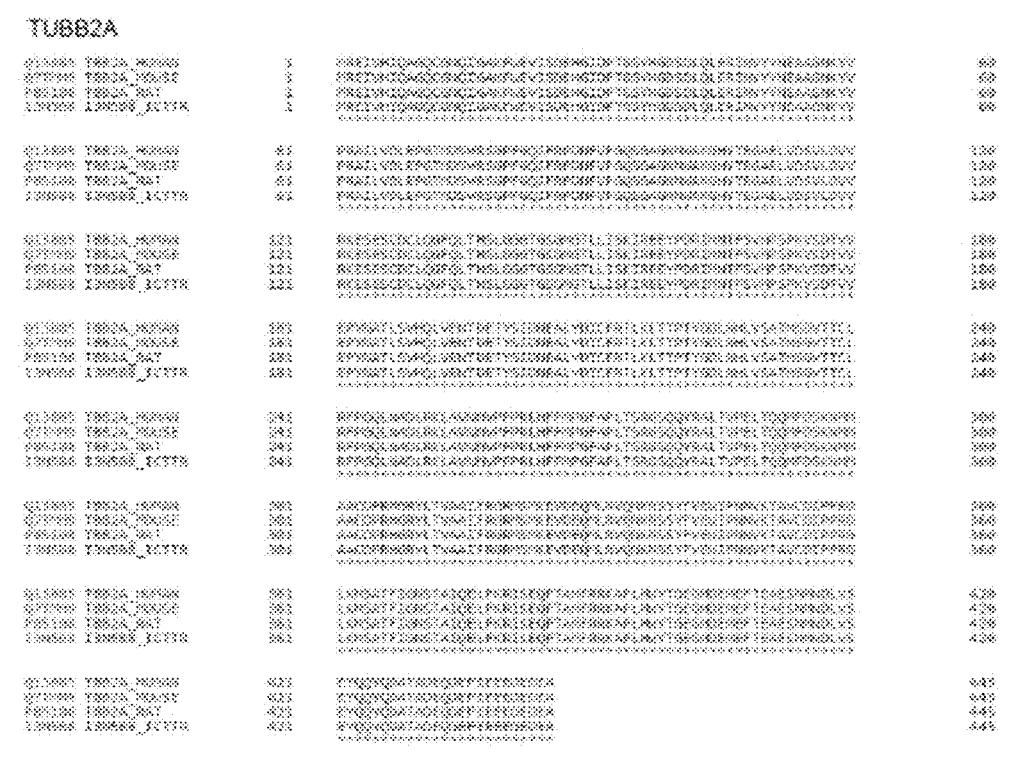
Figure 13E:
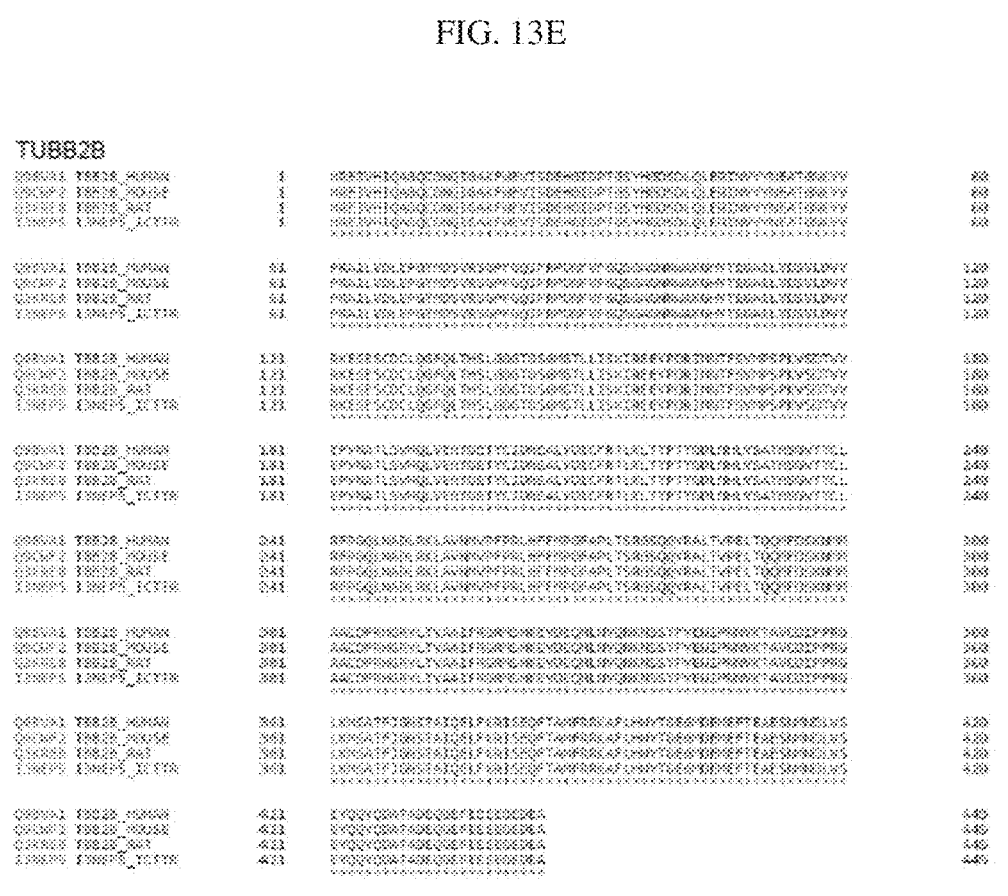
Figure 13F:
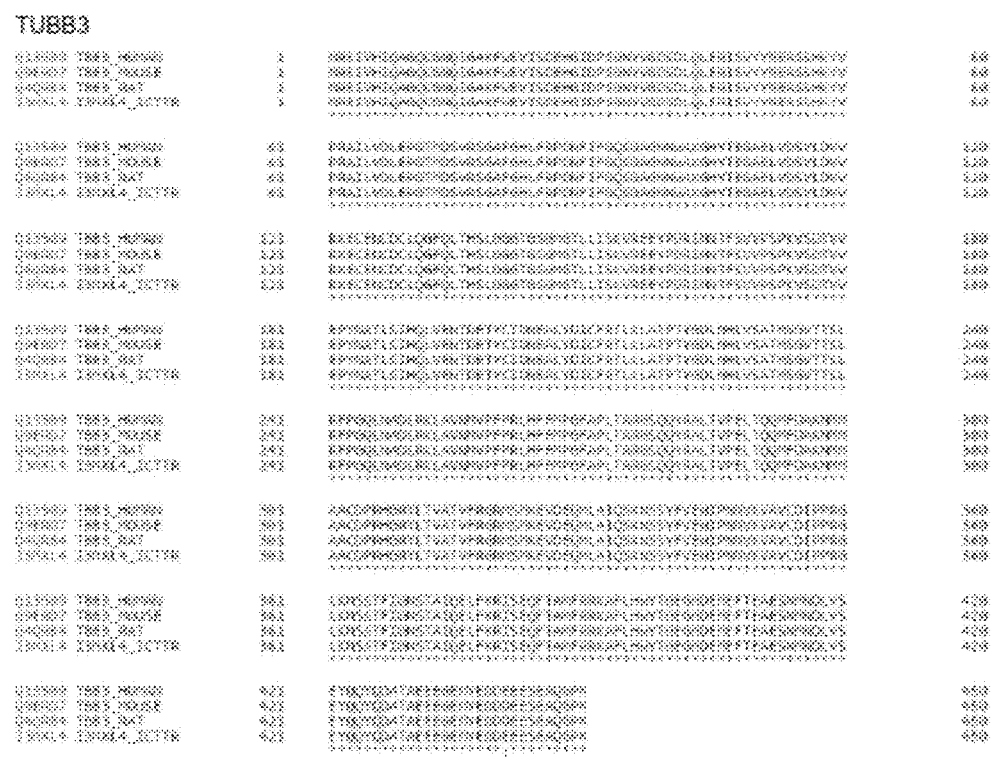
Figure 13G:
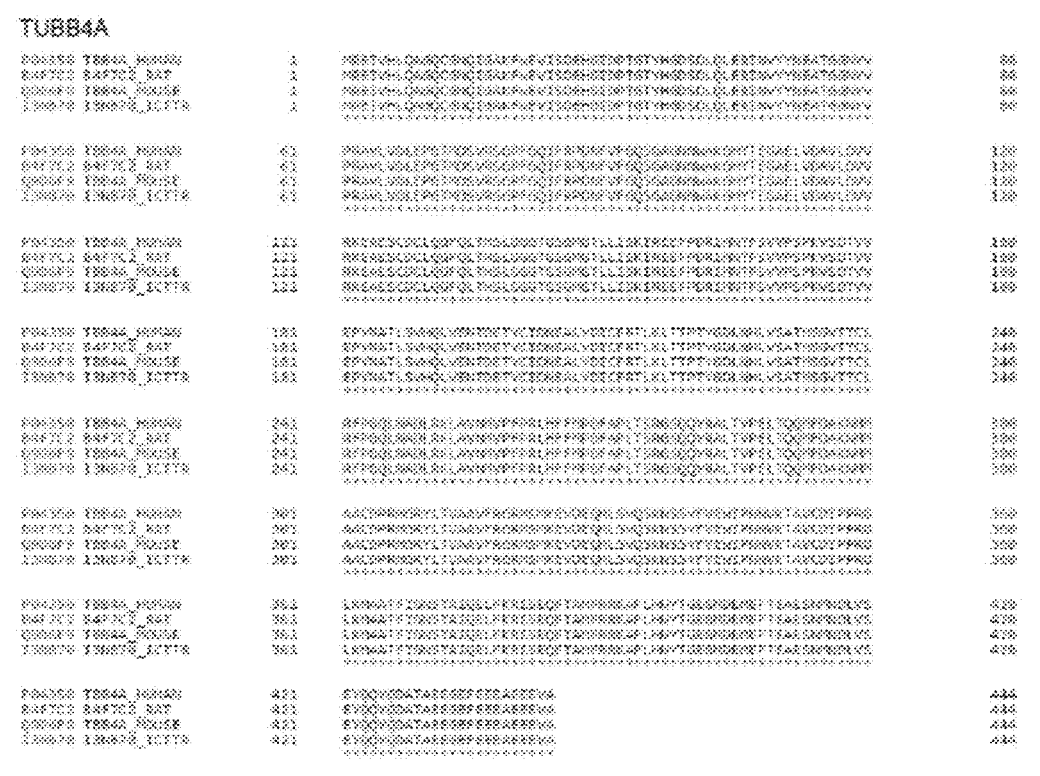
Figure 13H:
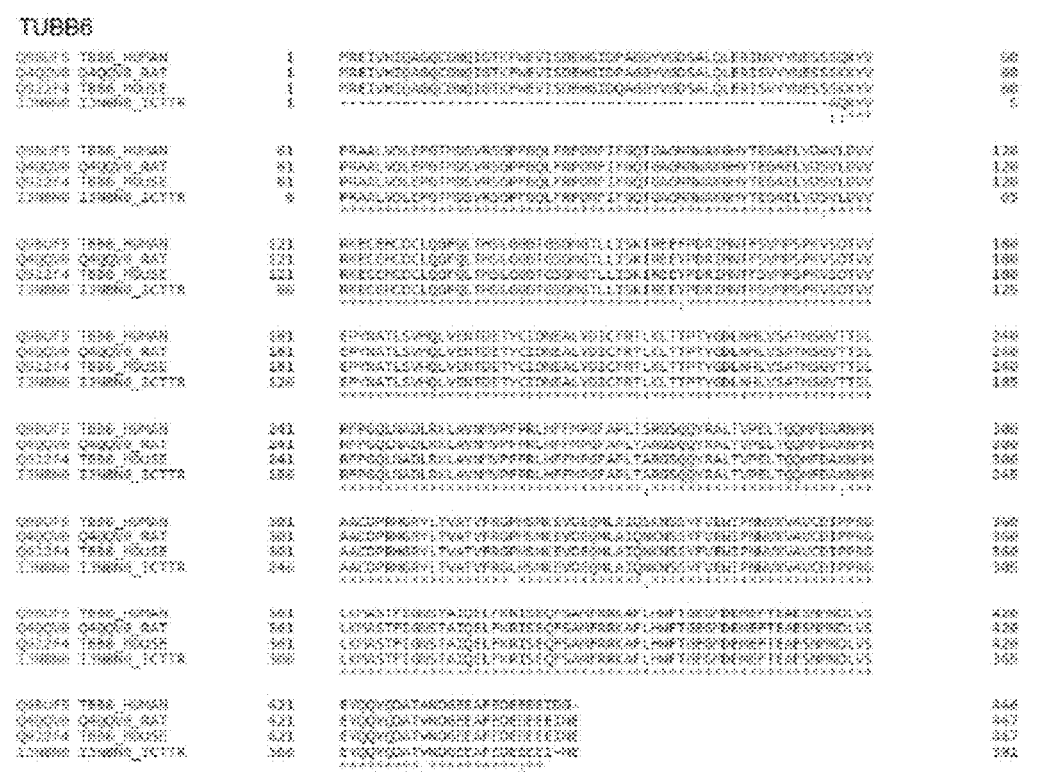

FIGS. 13A to 13H depict alignment of predicted protein sequences of tubulin genes identified in the transcriptome of GS iPSC-neurons.

DETAILED DESCRIPTION OF THE INVENTION

Terminology

Figure 1A:
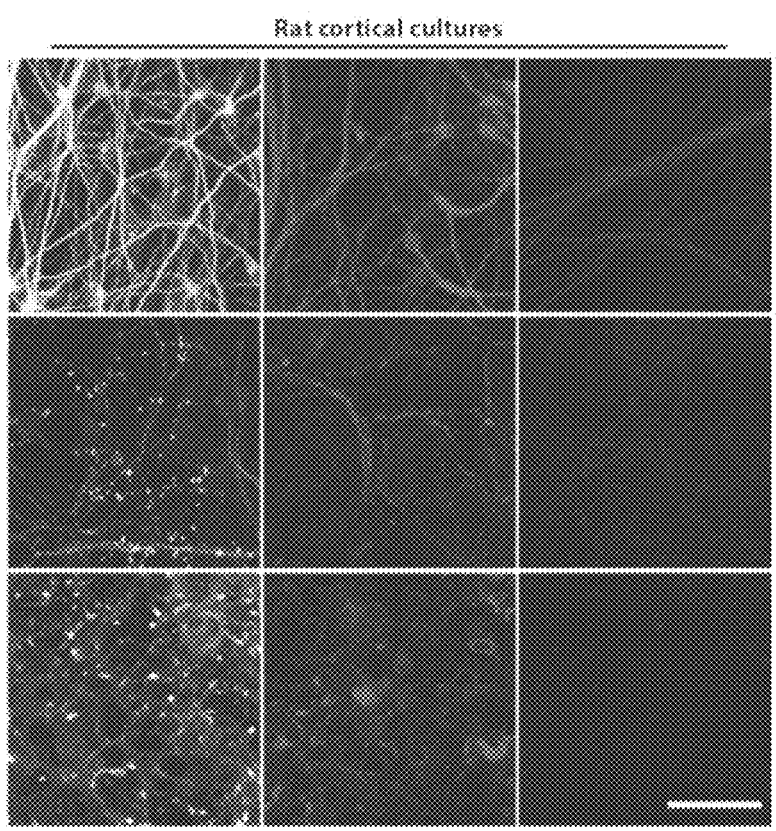
FIGS. 1A to 1G depict species-dependent differences in microtubule stability and transcriptome responses to prolonged cold exposure.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising", "having", "including", and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers and encompass heavy isotopes and radioactive isotopes. By way of general example, and without limitation, isotopes of hydrogen include tritium and deuterium, and isotopes of carbon include $^{11}C$, $^{13}C$, and $^{14}C$. Accordingly, the compounds disclosed herein may include heavy or radioactive isotopes in the structure of the compounds or as substituents attached thereto. Examples of useful heavy or radioactive isotopes include $^{18}F$, $^{15}N$, $^{18}O$, $^{76}Br$, $^{125}I$ and $^{131}I$.

The opened ended term "comprising" includes the intermediate and closed terms "consisting essentially of" and "consisting of".

A dash ("-") that is not between two letters or symbols is used to indicate a point of attachment for a substituent.

"Pharmaceutical compositions" means compositions comprising at least one active agent, such as a compound or salt having Formula 3, and at least one other substance, such as a carrier. Pharmaceutical compositions meet the U.S. FDA's GMP (good manufacturing practice) standards for human or non-human drugs.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any disease symptom, slow disease progression or cause disease regression. In certain embodiments treatment of the disease may be commenced before the patient presents symptoms of the disease.

A "physiologically effective amount" of a pharmaceutical composition means an amount effective, when administered to a patient, to provide a therapeutic benefit such as an amelioration of symptoms, decrease disease progression, or cause disease regression.

A "therapeutically active ingredient" means a compound which can be used for diagnosis or treatment of a disease. The compounds can be small molecules, peptides, proteins, or other kinds of molecules.

A significant change is any detectable change that is statistically significant in a standard parametric test of statistical significance such as Student's T-test, where $p<0.05$.

Embodiments

The nervous system of non-hibernating mammals is intrinsically unable to withstand severe cold conditions, as low temperature irreversibly damages the neuronal microtubules that vital neuronal activities rely on. It has been unexpectedly discovered that by targeting the activities of mitochondria and the protein degradation machineries with a novel composition described herein, the cold-sensitive mammalian tissue can survive and recover after a certain period of cold stress.

Thus, embodiments of the present invention are directed to a composition for preserving viability of cells, tissues, or organs during exposure to a low temperature environment. The composition includes a mitochondrial uncoupling agent, at least one protease inhibitor, and a reducing agent.

The composition, according to an embodiment, may include a mitochondrial uncoupling agent. Mitochondria are central to metabolism of the cells. They provide both energy to sustain biological activities and metabolic intermediates such as pyruvate, glycerol, and fatty acids for biosynthesis. Pyruvate is a metabolite which is formed through glycolysis of glucose. Pyruvate enters mitochondria, where it converts to acetyl-coenzyme A ("acetyl-CoA"). Glycerol and fatty acid are formed as a result of the triglyceride hydrolysis.

These metabolites enter mitochondria, where they are oxidized to acetyl-CoA. In mitochondrial matrix, acetyl-CoA are then oxidized through tricarboxylic acid ("TCA cycle"), and the energy released from the oxidation is stored in the form of high energy electrons in the molecules of nicotinamide adenine dinucleotide ("NADH") and flavine adenine dinucleotide ("FADH$_2$"). Electrons from NADH and FADH$_2$ are in turn fed into the mitochondrial electron transporter chain, which are situated on the inner membrane of mitochondria. As the electrons travel through the electron transporter chain and reach the electron receptor, which is oxygen molecule, energy is released and used for pumping protons from mitochondrial matrix across the mitochondrial inner membrane, establishing a proton gradient across the membrane. Finally, protons travel across the mitochondrial inner membrane through the F$_0$F$_1$-ATP synthase and drive the synthesis of ATP, the energy molecule that can be directly used by the various cellular components. Mitochondrial oxidation also provides and regulates the availability of metabolic intermediates required for biosynthesis of RNA, DNA, and lipids.

Generally, mitochondrial oxidation of acetyl-CoA and ATP synthesis are coupled in response to cellular energy needs. However, mitochondrial oxidation can be decoupled from ATP synthesis by mitochondrial uncouplers. Mitochondrial uncouplers facilitate the inward translocation of protons across mitochondrial inner membrane, thus dissipate or reduce the proton gradient without generating ATP.

In an embodiment, the mitochondrial uncoupling agent may be a compound represented by Formula 1:

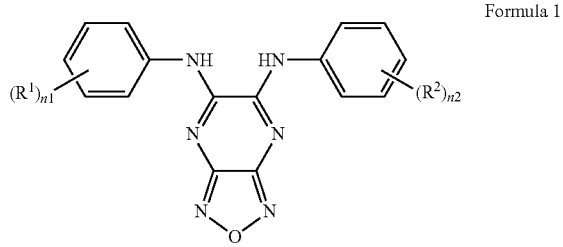

Formula 1 wherein

R$^1$ and R$^2$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{30}$ alkyl group, a substituted or unsubstituted C$_2$-C$_{30}$ alkenyl group, a substituted or unsubstituted C$_2$-C$_{30}$ alkynyl group, a substituted or unsubstituted C$_1$-C$_{30}$ alkoxy group, a substituted or unsubstituted C$_3$-C$_{30}$ cycloalkyl group, a substituted or unsubstituted C$_1$-C$_{30}$ heterocycloalkyl group, a substituted or unsubstituted C$_3$-C$_{30}$ cycloalkenyl group, a substituted or unsubstituted C$_1$-C$_{30}$ heterocycloalkenyl group, a substituted or unsubstituted C$_6$-C$_{30}$ aryl group, a substituted or unsubstituted C$_6$-C$_{30}$ aryloxy group, a substituted or unsubstituted C$_6$-C$_{30}$ arylthio group, a substituted or unsubstituted C$_7$-C$_{30}$ arylalkyl group, a substituted or unsubstituted C$_1$-C$_{30}$ heteroaryl group, a substituted or unsubstituted C$_2$-C$_{30}$ heteroaryloxy group, a substituted or unsubstituted C$_2$-C$_{30}$ heteroarylthio group, a substituted or unsubstituted C$_3$-C$_{30}$ heteroarylalkyl group, and —Si(Q$_1$)(Q$_2$)(Q$_3$), wherein Q$_1$ to Q$_3$ are each independently selected from a hydrogen, a C$_1$-C$_{30}$ alkyl group, a C$_1$-C$_{30}$ alkoxy group, a C$_3$-C$_{30}$ cycloalkyl group, a C$_1$-C$_{30}$ heterocycloalkyl group, a C$_3$-C$_{30}$ cycloalkenyl group, a C$_1$-C$_{30}$ heterocycloalkenyl group, a C$_6$-C$_{30}$ aryl group, and a C$_1$-C$_{30}$ heteroaryl group; and n1 and n2 are each independently an integer from 1 to 5.

In another embodiment, the mitochondrial uncoupling agent may be a compound represented by Formula 2:

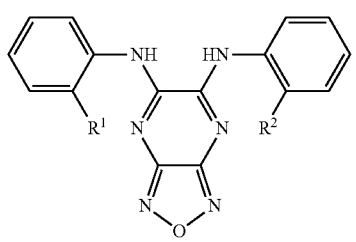

Formula 2 wherein R$^1$ and R$^2$ are the same as those described in connection with Formula 1.

In an embodiment, R$^1$ and R$^2$ may be each independently a hydrogen, —F, —Cl, —Br, or —I. For example, the mitochondrial uncoupling agent may be a compound having Formula 3:

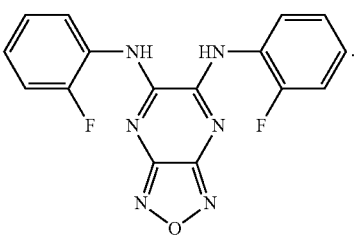

Formula 3

The composition may further include at least one protease inhibitor. A protease inhibitor is a substance that prevents viral replication by selectively binding to proteases and blocking proteolytic cleavage of protein precursors that are necessary for the production of infectious viral particles. The protease inhibitor, according to an embodiment, may be a cysteine protease inhibitor, an aspartic protease inhibitor, a serine protease inhibitor, a leucine aminopeptidase inhibitor, or a combination of these inhibitors, but is not limited thereto.

For example, the cysteine protease inhibitor may be (1S,2S)-2-(((S)-1-((4-guanidinobutyl)amino)-4-methyl-1-oxopentan-2-yl)carbamoyl)cyclopropanecarboxylic acid ("E-64"), which has the following structure:

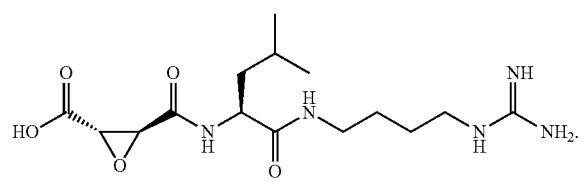

E-64

The aspartic protease inhibitor may be a peptide having a sequence Iva-Val-Val-Sta-Ala-Sta ("Pepstatin A"), which has the following structure:

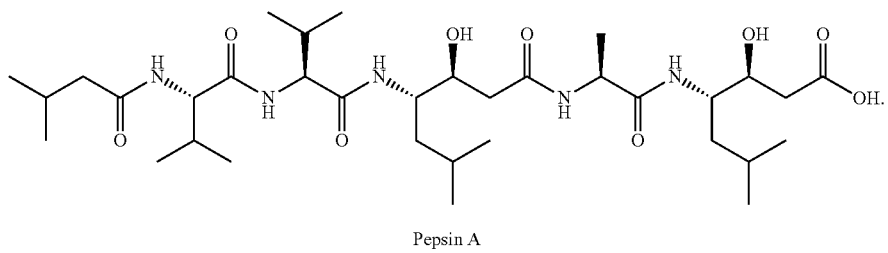 [SMILES: CC(C)CC(=O)N[C@H](C(=O)N[C@H](C(=O)N[C@@H](CC(C)C)[C@@H](O)CC(=O)N[C@@H](C)C(=O)N[C@@H](CC(C)C)[C@@H](O)CC(=O)O)C(C)C)C(C)C]

Pepsin A

The serine protease inhibitor may be 4-(2-aminoethyl)benzenesulfonyl fluoride ("AEBSF"), which has the following structure:

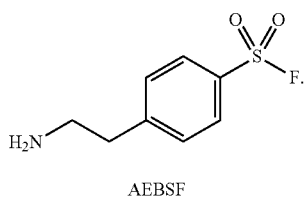 [SMILES: NCCc1ccc(S(=O)(=O)F)cc1]

AEBSF

The leucine aminopeptidase inhibitor may be (2S)-2-[[(2S,3R)-3-amino-2-hydroxy-4-phenylbutanoyl]amino]-4-methylpentanoic acid ("Bestatin"), which has the following structure:

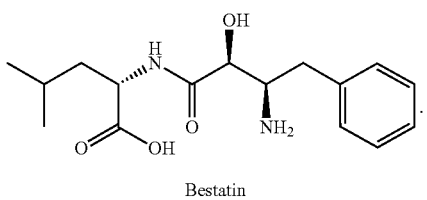 [SMILES: CC(C)C[C@H](NC(=O)[C@@H](O)[C@H](N)Cc1ccccc1)C(=O)O]

Bestatin

The composition may further include a reducing agent, which may be naturally occurring or non-naturally occurring. For example, the naturally occurring reducing agent may be glutathione, vitamin E, or ascorbic acid having the following structure:

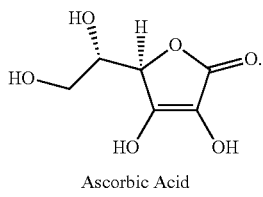 [SMILES: O=C1O[C@H]([C@@H](O)CO)C(O)=C1O]

Ascorbic Acid

Examples of non-naturally occurring reducing agents may include 1,4-dithiothreitol ("DTT") and beta-mercaptoethanol.

The concentration of the mitochondrial uncoupling agent in the composition may be about 50 to 200 nanomolar (nM), for example, about 75 to about 150 nM, or about 100 nM.

The concentration of the at least one protease inhibitor in the composition may be about 0.1 to about 50 micromolar (µM), for example, about 1 to about 25 µM, or about 10 to about 20 µM.

The concentration of the reducing agent in the composition may be about 50 to 300 µM, for example, about 100 to about 200 µM, or about 150 µM.

The composition may further include a pharmaceutically acceptable excipient. A pharmaceutically acceptable excipient, as used herein, refers to a non-active pharmaceutical ingredient ("API") substance such as a disintegrator, a binder, a filler, and a lubricant used in formulating pharmaceutical products. Each of these substances is generally safe for administering to humans according to established governmental standards, including those promulgated by the United States Food and Drug Administration ("FDA").

A disintegrator, as used herein, refers to one or more of agar-agar, algins, calcium carbonate, carboxymethylcellulose, cellulose, clays, colloid silicon dioxide, croscarmellose sodium, crospovidone, gums, magnesium aluminium silicate, methylcellulose, polacrilin potassium, sodium alginate, low substituted hydroxypropylcellulose, and cross-linked polyvinylpyrrolidone hydroxypropylcellulose, sodium starch glycolate, and starch, but is not limited thereto.

A binder, as used herein, refers to one or more of microcrystalline cellulose, hydroxymethyl cellulose and hydroxypropylcellulose, but is not limited thereto.

A filler, as used herein, refers to one or more of calcium carbonate, calcium phosphate, dibasic calcium phosphate, tribasic calcium sulfate, calcium carboxymethylcellulose, cellulose, dextrin derivatives, dextrin, dextrose, fructose, lactitol, lactose, magnesium carbonate, magnesium oxide, maltitol, maltodextrins, maltose, sorbitol, starch, sucrose, sugar, and xylitol, but is not limited thereto.

A lubricant, as used herein, refers to one or more of agar, calcium stearate, ethyl oleate, ethyl laureate, glycerin, glyceryl palmitostearate, hydrogenated vegetable oil, magnesium oxide, magnesium stearate, mannitol, poloxamer, glycols, sodium benzoate, sodium lauryl sulfate, sodium stearyl, sorbitol, stearic acid, talc, and zinc stearate, but is not limited thereto.

The composition may be administered to protect a patient during the surgery and to improve the effect of therapeutic hypothermia in a patient. The composition may be administered to a patient by oral, parenteral (e.g., intramuscular, intraperitoneal, intravenous, ICV, intracisternal injection or infusion, subcutaneous injection, or implant), by inhalation spray, nasal, sublingual, or topical routes of administration and may be formulated, alone or together, in suitable dosage unit formulations containing conventional non-toxic pharmaceutically acceptable carriers, adjuvants and vehicles appropriate for each route of administration. The method of administration may vary as needed. For example, for general administration, infusion may be found to be a preferred method of administration. For patients undergoing brain surgery, intracisternal injection would probably be the most efficient. The compounds of the invention are suitable for the treatment of warm-blooded animals (e.g., mice, rats, horses, cattle, sheep, dogs, cats, monkeys, etc.) and are effective for use in humans. As used herein, the terms "administration of" and or "administering a" compound should be understood to mean providing a compound of the invention or a prodrug of a compound of the invention to the individual in need of treatment.

The composition intended for oral use may be prepared according to any method known to the art for the manufacture of pharmaceutical compositions, and such compositions may contain one or more agents including for example sweetening agents, flavoring agents, coloring agents and preserving agents in order to provide pharmaceutically elegant and palatable preparations. Tablets contain the therapeutically active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the therapeutically active ingredients are mixed with an inert solid diluent, for example, calcium carbonate, calcium phosphate or kaolin, or as soft gelatin capsules wherein the therapeutically active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. Compositions containing a compound of the invention, or pharmaceutically acceptable salts thereof, can also be prepared in powder or liquid concentrate form.

In another embodiment, the invention is also directed to a method for treating mammalian cells, tissues, or organs to withstand exposure to a low temperature environment during therapy, treatment, or a medical procedure. The method comprises the steps of (1) providing mammalian cells, tissues, or organs to be exposed to a low temperature environment; (2) providing a composition comprising a mitochondrial uncoupling agent, at least one protease inhibitor, and a reducing agent; and (3) contacting the mammalian cells, tissues, or organs with the composition to enable the mammalian cells, tissues, or organs withstand exposure to a low temperature environment. This method finds utility in any therapy, treatment, or medical procedure that involves exposing cells, tissues, or organs to a low temperature environment. Examples of such therapy, treatment, or medical procedures include, but are not limited to, organ or cellular transplantation, hypothermia, hibernation, or storage of organs, tissues, or cells, and the like.

According to the method, the mammalian cells, tissues, or organs are contacted with a composition including a mitochondrial uncoupling agent, at least one protease inhibitor, and a reducing agent, which is described in detail above.

The composition may be obtained by combining individually prepared mixtures of mitochondrial uncoupling agent, the at least one protease inhibitor, and the reducing agent in a solvent medium. The solvent medium may be water or any medical aqueous buffer, such as artificial tear solution, artificial cerebrospinal fluid, and saline, but is not limited thereto.

The mitochondrial uncoupling agent may be a compound represented by Formula 1:

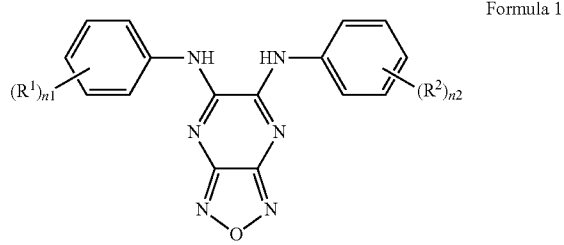

Formula 1 wherein
$R^1$ and $R^2$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_1$-$C_{30}$ heterocycloalkyl group, a substituted or unsubstituted $C_3$-$C_{30}$ cycloalkenyl group, a substituted or unsubstituted $C_1$-$C_{30}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_7$-$C_{30}$ arylalkyl group, a substituted or unsubstituted $C_1$-$C_{30}$ heteroaryl group, a substituted or unsubstituted $C_2$-$C_{30}$ heteroaryloxy group, a substituted or unsubstituted $C_2$-$C_{30}$ heteroarylthio group, a substituted or unsubstituted $C_3$-$C_{30}$ heteroarylalkyl group, and —Si($Q_1$)($Q_2$)($Q_3$), wherein $Q_1$ to $Q_3$ are each independently selected from a hydrogen, a $C_1$-$C_{30}$ alkyl group, a $C_1$-$C_{30}$ alkoxy group, a $C_3$-$C_{30}$ cycloalkyl group, a $C_1$-$C_{30}$ heterocycloalkyl group, a $C_3$-$C_{30}$ cycloalkenyl group, a $C_1$-$C_{30}$ heterocycloalkenyl group, a $C_6$-$C_{30}$ aryl group, and a $C_1$-$C_{30}$ heteroaryl group; and n1 and n2 are each independently an integer from 1 to 5.

The at least one protease inhibitor may include a cysteine protease inhibitor, an aspartic protease inhibitor, a serine protease inhibitor, a leucine aminopeptidase inhibitor, or a combination thereof. The reducing agent may be ascorbic acid.

In an embodiment, the mitochondrial uncoupling agent may be a compound having Formula 3:

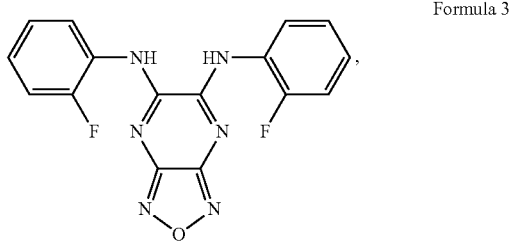 [SMILES: Fc1ccccc1Nc1nc2nonc2nc1Nc1ccccc1F]

Formula 3 the at least one protease inhibitor may be a combination of E-64, Pepstatin A, AEBSF, and Bestatin, and
the reducing agent may be ascorbic acid.

The composition for cells, tissues and organs preservation may be used by dissolving in any physiological solutions deemed suitable for the target cells, tissues and organs, or may be combined with a commercially available cryopreservation agent prior to contacting the mammalian cells. Examples of commercially available cryopreservation agents may include Optisol GS and similar agents for human cornea cold storage, University of Wisconsin (UW) Solution and similar agents for liver and kidney cold storage, and HypoThermosol®, but are not limited thereto. In an embodiment, the composition may be mixed with these commercially available solutions prior to contacting the cells. When not commercially available, the treatment solution may be prepared by directly dissolving the composition (in this invention) into a known or experimental cryopreservation agent to a concentration to be optimized for the target cells, tissues or organs.

The mammalian cells, tissues, or organs that may be treated according to the compositions and methods of the invention include neuronal cells, retinal cells, cornea, retina, skin, heart, lung, pancreas, kidney, liver, intestine, stem cells, blood, or any other cell, tissue, or organ that is suitable for transplantation. These cells/tissues/organs are transplantable and are commonly stored at 0-5° C. before transplantation. The cells may be contacted with a composition at a temperature of 22° C. to 37° C., for example, 25° C. to 37° C., or 22° C. to 35° C. Exemplary contacting times may include 5 minutes to 5 weeks (in the case of cornea), for example, 30 to 60 minutes, 1 hour to 35 days, 4 hours to 35 days, 8 hours to 35 days, 16 hours to 35 days, 1 day to 35 days, 2 days to 35 days, 3 days to 35 days, or 4 days to 35 days.

The contacted cells may then be maintained at a temperature of 5° C. or lower, for example, 4° C. or lower, 3° C. or lower, or 2° C. or lower to preserve the cells for transplantation. In some embodiments, the contacted cells may be maintained at a temperature of 1° C. to 5° C., for example, 1° C. to 2° C., 2° C. to 3° C., 3° C. to 4° C., or 4° C. to 5° C.

The contacted cells may be maintained for 4 to 72 hours, for example, for 4 to 6 hours, for 8 to 24 hours, or for 24 to 72 hours. The contacted tissues or organs may be administered with the agents and maintained viability for 1 to 35 days at a temperature of 1° C. to 5° C., in their suitable storage solution currently used in clinical practice.

In an embodiment, the maintenance of the contacted cells at a temperature from 2° C. to 5° C. for 6 hours may results in preservation of about 80 to 100% of neuronal morphology of the cells. In another embodiment, the maintenance of the contacted cells at a temperature from 2° C. to 5° C. for 24 hours may result in preservation of about 30 to 40% of neuronal morphology of the cells.

In another embodiment, a method for transplantation of mammalian cells, tissues, or organs is provided. The method includes the steps of:

providing a composition comprising a mitochondrial uncoupling agent, at least one protease inhibitor, and a reducing agent;

contacting the mammalian cells, tissues, or organs with the composition;

maintaining the contacted cells, tissues, or organs at a temperature of 5° C. or lower to preserve the cells, tissues, or organs; and carrying out transplantation of the preserved cells, tissues, or organs.

In another embodiment, a method for protecting a mammal against hypothermia is provided. The method includes the steps of:

providing a composition comprising a mitochondrial uncoupling agent, at least one protease inhibitor, and a reducing agent;

administering a physiologically effective amount of the composition to the mammal; and exposing the mammal to an environment having a temperature of 5° C. or lower.

In another embodiment, a method for inducing hibernation in a non-hibernating mammal is provided. The method includes the steps of:

providing a composition comprising a mitochondrial uncoupling agent, at least one protease inhibitor, and a reducing agent;

administering a physiologically effective amount of the composition to the mammal; and inducing hibernation in the mammal.

In another embodiment, a method for protecting a mammal's cells, tissues, or organs during therapeutically induced hypothermia is provided. The method includes the steps of:

providing a composition comprising a mitochondrial uncoupling agent, at least one protease inhibitor, and a reducing agent;

administering a physiologically effective amount of the composition to the mammal; and inducing a therapeutic hypothermia in the mammal.

In another embodiment, a method of preserving neural cells, tissues, or organs of a patient during therapeutic hypothermia is provided. The method includes administering a physiologically effective amount of the composition, according to an embodiment, to the patient prior to induction of therapeutic hypothermia.

The present invention is illustrated and further described in more detail with reference to the following non-limiting examples.

Examples

Methods and Materials
Preparation of Composition

A solution of 0.05 to 0.2 µM of the compound represented by Formula 3 in a suitable medium, 3 to 5 µM of E-64 in the medium, 2 to 4 µM of Pepstatin A in the medium, 100 to 200 µM of AEBSF in the medium, 10 to 20 µM of Bestatin in the medium, and 50 to 200 µM of ascorbic acid in the medium are combined to form a composition.

Animals

Adult 13-lined ground squirrel (GS) colonies were maintained at the animal facility of the National Eye Institute in accordance with the requirements of our institutional Animal Review Board. Pregnant ground squirrels and newborn pups were provided courtesy of Prof. Dana Merriman at the University of Wisconsin-Oshkosh. Post-mortem rat retinas were obtained from healthy adult Sprague Dawley rats of 2-6 months old and provided by the animal facility of the National Institute of Neurological Disorders and Stroke (NINDS), National Institutes of Health (NIH). Post-mortem mouse kidneys were obtained from healthy adult C57BL/6J mice of 2-12 months old and provided by the animal facility of NINDS. All animal procedures were approved by the Institutional Animal Care and Use Committee of the National Eye Institute and conform to the provisions of the Animal Welfare Act (NIH/DHHS).

Cell Isolation

Cortical tissues from postnatal day 0-2 GS pups were dissected and then dissociated using a neural tissue dissociation kit (Miltenyi Biotech, San Diego, Calif.). Neural precursor cells were then purified with magnetic activated cell sorting using magnetic anti-PSA-NCAM microbeads, myelin removal beads, and FcR blocking reagent (Miltenyi Biotech, San Diego, Calif.). Purified cells were expanded prior to transduction. Primary cultures of rat and GS cortical neurons were maintained following the protocol described in (Meberg, 2003).

Cell Culture and Reprogramming

All cell culture media reagents were used as directed in the manufacturer's instructions unless otherwise specified; the reagents are listed in Table 1. GS cell culture protocols were adapted from the following sources describing human cell culture protocols stemcells.nih.gov/research/nihresearch/scunit/protoc ols.htm) with the following modifications: the purified GS NPCs were cultured in 5% Matrigel-coated dishes in Neural Precursor Cell (NPC) medium until 70-80% confluence was reached. The NPCs were then transfected with the Cytotune-iPS 2.0 Sendai Reprogramming kit (Thermo Fisher Scientific, Waltham, Mass.) for 24 hours. The transfected NPCs were dissociated by accutase and passaged into new 5% matrigel-coated wells at a 1:3 ratio in iPSC maintenance medium. After 5-7 days, flat colonies emerged and were manually picked or lifted off with dispase digestion, mechanically dissociated with gentle pipetting, and passaged to a new Matrigel-coated culture well.

TABLE 1

Antibodies and Reagents, Related to Methods.

| Primary Abs. | Supplier | Catalog # | Application | Dilution | Species |
|---|---|---|---|---|---|
| Poly-E-T | AdipoGen | AG-20B-0020-C100 | IF | 1:1000 | Mouse IgG1 |
| TUBB3 | R & D systems | MAB1195 | IF | 1:1000 | Mouse IgG2a |
| OCT-3/4 | Santa Cruz | sc-5279 | IF | 1:500 | Mouse IgG2b |
| NANOG | Cosmo Bio | RCAB0004P-F | IF | 1:500 | Rabbit |
| ALBUMIN | Cedarlane | CL2513A | IF | 1:500 | Mouse IgG1 |
| HNF4 | Cell Signaling | 3133 | IF | 1:500 | Rabbit |
| DESMIN | Thermo Fisher | RB9014P1 | IF | 1:500 | Rabbit |
| TNNT | Thermo Fisher | MS295P0 | IF | 1:500 | Mouse IgG1 |
| A2-T | Millipore | AB3203 | WB & IF | 1:1000 | Rabbit |
| Poly-E-T | AdipoGen | AG-25B-0030-C050 | WB | 1:2000 | Rabbit |
| TUBB3 | BioLegend | 802001 | WB | 1:2000 | Rabbit |
| TUBA | Sigma | F2168 | IF | 1:200 | Mouse IgG1 |
| LAMP1 | Cell Signaling | 9091 | WB | 1:1000 | Rabbit |
| VCP (p97) | Cell Signaling | 2648 | WB | 1:1000 | Rabbit |
| VCP (p97) | Fitzgerald | 10R-P104a | WB | 1:5000 | Mouse IgG1 |
| PSMB2 | Santa Cruz | SC-515066 | WB | 1:1000 | Mouse IgG1 |
| PSMB5 | Santa Cruz | SC-393931 | WB | 1:1001 | Mouse IgG2a |
| HSP40 | Cell Signaling | 4868 | WB | 1:1000 | Rabbit |
| HSP60 | Santa Cruz | SC-13115 | WB | 1:1000 | Mouse IgG3 |
| HSP70 | Santa Cruz | sc-7298 | WB | 1:1000 | Mouse IgG2a |
| HSP90 | Santa Cruz | sc-13119 | WB | 1:1000 | Mouse IgG2a |
| β-actin | Cell Signaling | 4970 | WB | 1:1000 | Rabbit |

| Other Reagents | Supplier | Catalog # | Concentration |
|---|---|---|---|
| Protein Oxidation Detection Kit | Millipore | S7150 | * |
| Proteostat Aggresome Detection Kit | Enzo Life Sciences | ENZ-51035 | * |
| MG-132 | Enzo Life Sciences | ENZ-51035 | 5 µM |
| BAM15 | Tocris | 5737 | 0.05-5 µM |
| Protease inhibitor cocktail set III (PI) | Millipore | 539134 | 1:500 |
| PYR-41 | Tocris | 2978 | 5-10 µM |
| Taxol | Tocris | 1097 | 0.1 or 10 µM |
| CellROX Green | Thermo Fisher | C10444 | 1 µM |
| TMRE | Thermo Fisher | T669 | 50 nM |
| pCMV6-XL5-TUBB3 | Origene | SC116313 | 4 µg/million cells |
| pCMV6-Myc-DDK-Tubb3 | Origene | MR207181 | 4 µg/million cells |
| LipoJet in vitro transfection kit | SignaGen Laboratories | SL100468 | * |
| Ames' medium | Sigma | A1420 | — |
| TRIzol | Thermo Fisher | 15596018 | — |
| RNeasy kit | Qiagen | 74104 | — |

TABLE 1-continued

Antibodies and Reagents, Related to Methods.

| | | | |
|---|---|---|---|
| TruSeq ® Stranded mRNA LT-Set A | Illumina | RS-122-2101 | — |
| NextSeq ® 500/550 High Output Kit v2 | Illumina | FC-404-2002 | — |
| Magic Red cathepsin B assay kit | ImmunoChemistry Tech. | 938 | 1:1000 |
| LysoTracker Green DND-26 | Thermo Fisher | L7526 | 50 nM |
| Click-iT lipid peroxidation imaging kit-Alexa Fluor 488 | Thermo Fisher | C10446 | 1:1000 |
| RIPA lysis and extraction buffer | Thermo Fisher | 89900 | — |

| University of Wisconsin Solution | Concentration (g/L) |
|---|---|
| Hydroxyethyl starch (Pentafraction) | 50.0 |
| Lactobionic acid (as Lactone) | 35.83 |
| Potassium dihydrogen phosphate | 3.4 |
| Magnesium sulfate heptahydrate | 1.23 |
| Raffinose pentahydrate | 17.83 |
| Adenosine | 1.34 |
| Allopurinol | 0.136 |
| Total Glutathione | 0.922 |
| Potassium hydroxide | 5.61 |
| Sodium hydroxide/Hydrochloric acid | adjust to pH 7.4 |

Pluripotency Validation of GS iPSCs

Pluripotency of GS iPSC colonies was characterized by alkaline phosphatase staining and OCT3/4/NANOG immunostaining. These antibodies are listed in Table 1. The pluripotency status of GS iPSCs was also evaluated by their ability to differentiate into all 3 germ layers in vitro using protocols found at stemcells.nih.gov/research/nihresearch/scunit/protoc ols.htm. Pluripotency was also verified in vivo using a standard teratoma formation assay (Applied StemCell, CA, USA).

Neuronal Differentiation of Human and Ground Squirrel iPSCs

Three different human iPSC-derived neural progenitor cell (NPC) lines were obtained from the Stem Cell Unit of the National Institutes of Health courtesy of Dr. Barbara Mallon. Human iPSC-derived neurons were cultured as described in stemcells.nih.gov/research/nihresearch/scunit/protoc ols.htm. The protocol for culturing GS iPSC-derived neuronal cultures were adapted from the above human cell culture protocol. Human and GS NPCs were first expanded in NPC medium for 3 days and then switched to neural differentiation medium (NDM) (Table 2) for at least 7 days resulting in a population of mature neurons and support cells. Experimental results were verified in all three human NPC lines. For GS neuronal differentiation, the first 2 days required GS NDM, afterwards the medium was changed to human NDM.

TABLE 3

Cell culture media formulations and reagents.

| iPSC Medium | Supplier | Catalog # | Concentration |
|---|---|---|---|
| DMEM/F12 | Thermo Fisher | 11320-033 | — |
| Knockout Serum Replacement | Thermo Fisher | 10828-028 | 15% |
| Non-Essential Amino Acids | Thermo Fisher | 11140-050 | 1x |
| L-Glutamine (200 mM) | Thermo Fisher | 25030-081 | 2 mM |
| B-Mercaptoethanol (5 mM in PBS) | Thermo Fisher | 21985-023 | 10 µM |
| b-FGF | R & D Systems | 233-FB-025 | 40 ng/mL |

TABLE 3-continued

Cell culture media formulations and reagents.

| Human NPC medium | Supplier | Catalog # | Concentration |
|---|---|---|---|
| DMEM | Thermo Fisher | 11965-044 | — |
| B27 supplement (50x), no VitA | Thermo Fisher | 12587010 | 1x |
| L-Glutamine (200 mM) | Thermo Fisher | 25030-081 | 2 mM |
| b-FGF | R & D Systems | 233-FB-025 | 20 ng/mL |
| Human NOGGIN | R&D Systems | 6057-NG | 10 ng/mL |
| Human EGF | R&D Systems | 236-EG | 20 ng/mL |

| GS NPC medium | Supplier | Catalog # | Concentration |
|---|---|---|---|
| DMEM | Thermo Fisher | 11965-044 | — |
| B27 supplement (50x), no VitA | Thermo Fisher | 12587010 | 1x |
| L-Glutamine (200 mM) | Thermo Fisher | 25030-081 | 2 mM |
| b-FGF | R&D Systems | 233-FB-025 | 20 ng/mL |
| Human NOGGIN | R&D Systems | 6057-NG | 10 ng/mL |
| Human EGF | R&D Systems | 236-EG | 20 ng/mL |
| Knockout Serum Replacement | Thermo Fisher | 10828-028 | 5% volume |

| Human ND medium | Supplier | Catalog # | Concentration |
|---|---|---|---|
| Neurobasal-A medium | Thermo Fisher | 10888022 | — |
| L-Glutamine (200 mM) | Thermo Fisher | 25030-081 | 2 mM |
| B27 supplement (50x) | Thermo Fisher | 17504044 | 1x |
| BDNF | R&D Systems | 248-BD | 10 ng/mL |
| GDNF | R&D Systems | 212-GD | 2.5 ng/mL |

TABLE 3-continued

Cell culture media formulations and reagents.

| GS ND medium (first 2 days) | Supplier | Catalog # | Concentration |
|---|---|---|---|
| Neurobasal-A medium | Thermo Fisher | 10888022 | — |
| L-Glutamine (200 mM) | Thermo Fisher | 25030-081 | 2 mM |
| B27 supplement (50x) | Thermo Fisher | 17504044 | 1x |
| BDNF | R&D Systems | 248-BD | 10 ng/mL |
| GDNF | R&D Systems | 212-GD | 2.5 ng/mL |
| Knockout Serum Replacement | Thermo Fisher | 10828-028 | 5% volume |
| Activin A | R&D Systems | 338-AC | 20 ng/mL |

| Hibernate medium | Supplier | Catalog # | Concentration |
|---|---|---|---|
| Hibernate A medium | BrainBits | HA | — |
| Neurobasal-A medium | Thermo Fisher | 25030-081 | 1:1 |
| B27 supplement (50x) | Thermo Fisher | 17504044 | 1x |
| L-Glutamine (200 mM) | Thermo Fisher | 25030-081 | 2 mM |
| Antibiotic-Antimycotic (100x) | Thermo Fisher | 15240062 | 1x |
| BDNF | R&D Systems | 248-BD | 10 ng/mL |
| GDNF | R&D Systems | 212-GD | 2.5 ng/mL |

Evaluation of Neuronal Microtubule Stability in Response to Cold

The temperature-dependent experiments in this study were performed at ambient $CO_2$ concentration, which required the use of hibernate-medium (Table 2) to maintain the physiological pH. Experiments were conducted by first incubating cultured neurons (human iPSC-derived, GS iPSC-derived, GS primary, or rat primary cultures) in hibernate-medium for 30 min at room temperature. During this time (pre-incubation), drug treatments (see Other Reagents, Table 1) were introduced to test cold resistance and microtubule stability. The cell culture dishes were then kept in an ambient 37° C. incubator, or in a 4° C. refrigerator. The temperature of the culture media incubated in the refrigerator was observed to decrease from 22° C. to 12° C. in 5 min and to 4° C. in 20 min. The pH of hibernate-medium was stable and maintained the pH between 7.0 and 7.4 even after 16-h incubation at 4° C.

Multielectrode Array (MEA) Measurements

All experiments were carried out under dim red light. Rat retina explants were removed and cut into smaller pieces in hibernate-medium, and divided into different treatment groups for pre-incubation with drugs promoting microtubule stability or a DMSO vehicle control at room temperature for 30 minutes. The cold-exposed groups were incubated in the refrigerator, while the fresh control samples were incubated on the bench in dark at room temperature. It has been shown that keeping enucleated eyes under hypothermic and ischemic conditions extends retinal viability in vitro (Reinhard, 2016; Schultheiss, 2016), as limited access to oxygen and nutrients might reduce mitochondrial metabolism and hence ROS production. Here the rat retinas were allowed to have full access to nutrients and oxygen in all experimental groups, hence low temperature was the only cause of stress in our experiments. After 4- or 24-hour incubation, the cold-exposed retinal explants were placed on the bench for 10-15 minutes, and washed twice with fresh hibernate-medium. Retinal explants from all groups were then transferred to oxygenated (95% $O_2$/5% $CO_2$) bicarbonate-buffered AMES medium at room temperature. The sclera and RPE were removed prior to flat mounting the neural retina with the ganglion cell (RGC)-side facing down onto the MEA.

During MEA recording, the neural retinas were perfused with 95% $O_2$/5% $CO_2$-balanced AMES perfusion at 37° C. to measure the spontaneous firing activity of the rat RGCs over the course of 15 minutes. To assess light responsiveness of the rat retina explants, the tissue was exposed to approximately 1-s flashes of light from either a bright white LED (Mightex, Pleasanton, Calif.) or a halogen lamp (OSRAM, Germany). For each retina, light-driven ganglion cell activity (action potential firing) was elicited in response to six flashes of light that were spaced at approximately either 10 or 15-s intervals. After the recording, the rat retinal explants were fixed with 4% paraformaldehyde for 2 h and then immunostained for neuronal tubulins. For MEA data processing and analyses, the firing spikes of RGCs were first filtered and recorded in MC Rack with a high-pass filter set at 200 Hz, a low-pass filter set at 3000 Hz, and the automatic standard deviation for spike detection threshold was set at −6. To remove false positives and to group spikes into clusters corresponding to individual cells, spike waveforms were sorted using Plexon Offline Sorter v. 3.3.5 (Plexon Inc., Dallas, Tex.). Spikes were automatically clustered into a maximum of eight units (cells) per electrode using the built-in K-means clustering algorithm. The analysis and identification of light responsiveness was performed in MATLAB rev. 2015a (The Mathworks, Natick, Mass.). Briefly, spike times were binned at 200 ms intervals, and the firing rates observed for a given cell during the first bin of each light flash were statistically compared to those during non-stimulated intervals. A cell was considered light-responsive if A) the stimulated spike rate was larger than the mean baseline firing rate and B) the outcome of a two-tailed, unequal variance t-test of these spike rates yielded a p-value <0.01. This test underestimates the number of light-responsive cells because it detects ON, but not OFF light responses. OFF responses were clearly visible in most MEA recordings, but they constituted a minority of cell types and were not quantified here.

Western Blotting and Immunostaining

All antibodies are listed in Table 1. RIPA buffer was used to lyse the cells and extract proteins (Thermo Fisher, Waltham, Mass.). Total proteins or proteins in the soluble fraction after standard centrifugation removing precipitates and debris were run on SDS-PAGE. Standard protocols were used for western blotting and immunostaining. For immunostaining of oxidized proteins, fixed cells were first incubated with 2,4-dinitrophenylhydrazine (DNPH), then stained with an antibody recognizing the DNPH-protein complex (Protein oxidation detection kit, see Table 1). All immunostaining and live cell confocal images were captured on a Zeiss LSM 510 system (Zeiss, Oberkochen, Germany). Western blots were quantified with the ImageJ Gel Analysis tool.

RNA-Seq Sample Preparation

GS and two different lines of human iPSC-derived neuronal cultures were maintained and prepared as described above. Experiments were conducted by first replacing NDM with fresh hibernate-medium and allowing the cultures to sit at room temperature for 30-min. The samples were divided into two groups: one was incubated in the refrigerator (4° C.) and the other in an ambient 37° C. incubator. Two incubation time points, 1 h and 4 h, were selected. Cells were collected and lysed in TRIzol (Thermo Fisher, Waltham, Mass.), total RNA were purified with RNeasy kit (Qiagen, Hilden, Germany), and further processed for RNA-sequencing (Illumina, San Diego, Calif.; see Table 1).

Mapping, Quantification and Differential Expression Analysis of RNA-Seq Data

After adapter trimming, raw reads were assessed using the FastQC toolset bioinformatics.babraham.ac.uk/projects/fastqc). Reads from different cell lines were aligned to the GS genome (Ensembl spetri2) (Yates, 2016) or to the human genome (UCSC hg19) (Speir, 2016) genome.ucsc.edu) separately with TopHat v2.1.1 (Trapnell, 2009) and allowed up to two mismatches per read for final read alignments. For quantification of gene expression, only the reads aligned to exons uniquely were counted using the R Subread package (Liao, 2013). A gene was included in further analysis if the maximum count-per-million >3 within any included samples. Given the pair-wise design of the experiments, negative binomial GLM fitting and testing for the effect of treatment by control of the effect of different cell lines were performed with embedded functions in DESeq2 (Love, 2014). P values from differential expression tests were adjusted using the Benjamini-Hochberg procedure for multiple hypothesis testing.

Functional Enrichment Analysis of Altered Transcripts

Gene Ontology (GO) analysis was performed based on hypergeometric test using Piano package (Varemo, 2013), with the gene list of interest as foreground, and all identified genes as background. The annotation of gene to GO terms was retrieved and localized from Ensembl database.

Tubulin Protein Sequence Homology Analysis

Tubulin protein sequences for genes (TUBA1C, TUBB2A, TUBB2B, TUBB/TUBB5, TUBA4A, TUBB3, TUBB4A, and TUBB6) of human, mouse, rat and 13-lined ground squirrel were obtained from Uniprot database (2015) and aligned using CLUSTAL Omega program (McWilliam, 2013). Canonical protein sequences were used when multiple isoforms were available.

Acetylation Prediction Analysis of Tubulin Proteins

For all tubulin proteins mentioned above, N-terminal and lysine acetylation events prediction was performed using NetAcet (Kiemer, 2005) and ASEB (Wang, 2012) separately. During prediction, complete protein sequences were submitted directly. In ASEB analysis, all available lysine acetylation transferases (KAT) families were explored. K-sites with P<0.05 were identified as acetylated.

Live Cell Imaging of Mitochondrial Membrane Potential (TMRE)

GS and human iPSC-derived neuronal cultures were prepared as described above. Experiments were conducted by first removing the neural differentiation medium and replacing it with hibernate-medium containing 50 nM TMRE (Thermo Fisher, Waltham, Mass.; see Table 1). At this time, 1) 0.1 µM of the compound having Formula 3 or 2) 1:500 dilution of protease inhibitor cocktail III (Millipore-Sigma, Darmstadt, Germany) were delivered to the two drug treatment groups. Cells were returned to the incubator and cultured for an additional 25 min at 37° C. Additional hibernate-medium matching these treatment conditions was stored in 50 mL conical tubes in either a 45° C. water bath or on ice to serve as a perfusion medium reservoir. Prior to imaging, TMRE-containing medium was discarded and replaced with fresh pre-warmed hibernate-medium. During the Z-stack time-lapse confocal imaging, the culture dish was continuously perfused; first with medium from the 45° C. reservoir for 5 min, and then switched to the ice-cold reservoir. This manipulation reduced the temperature of the medium in the culture dish to 10° C. (the lowest temperature the perfusion system could attain). Cells in the field of view were refocused, and the same Z-stack, time-lapse confocal images were taken for another 5 min. A maximum intensity projection of the Z-stack images was produced for data analysis. Temperature-dependent TMRE fluorescence increases were corrected under the assumption that the total TMRE molecules absorbed into each cell should remain relatively constant within the 10-min imaging duration. Thus, the whole cell area was initially selected as the region of interest (ROI) to estimate the temperature dependent contribution of the TMRE dye's fluorescence. To do this, the average TMRE fluorescence intensity was calculated from 10 frames of the 10° C. recording and divided that by the average TMRE fluorescence intensity from 10 frames of the 37° C. recording ($F_{c-10}/F_{c-37}$). The mitochondrial areas from the same cells were then selected as ROIs to measure the mitochondrial TMRE intensity at 37° C. ($F_{c-37}$) and 10° C. ($F_{m-10}$). The corrected mitochondrial TMRE intensity at 10° C. was calculated using the following equation: $F_{c \cdot m-10} = F_{m-10}/(F_{c-10}/F_{c-37})$. The percentage change in mitochondrial TMRE intensity change at 10° C. was thus calculated as: $(F_{c \cdot m-10} - F_{m-37})/F_{m-37} \times 100\%$. At least 5 different well-focused imaged cells per experiment were measured.

Live Cell Imaging of Oxidative Stress Using Cell CellROX-Green

GS and human iPSC-derived neuronal cultures were prepared in duplicate and pretreated with 1 µM CellROX-green (Thermo Fisher, Waltham, Mass.; see Table 1) with the appropriate drug treatments or vehicle as described above. To explore the influence of cold stress on ROS production, cells were either maintained at 37° C. (serving as normal controls) or exposed to 4° C. Cells were maintained for 30-min at 37° C., acclimated to room temperature on the bench for 5 min before being placed in a 4° C. refrigerator for 30 min. Cells were then gradually rewarmed at room temperature on the bench for 5 min prior to returning to 37° C. Z-stack confocal images were then obtained from the two groups at 37° C. Specifically, since CellROX-green only becomes fluorescent upon oxidation and DNA-binding this method avoids temperature-dependent dye fluorescent artifacts that accompany imaging at different temperatures while recording the cumulative production of ROS. Maximum intensity projections of the Z-stack images were produced for data analysis. At least 5 different well-focused imaged areas from each experiment were measured. Preliminary experiments also indicated that prior to incubation at either 37° C. or 4° C., the two groups of cultures had no difference in CellROX-green fluorescent intensity (data not shown).

Live Cell Imaging of Lysosomes Using Magic Red and DND-26

GS and Human iPSC-derived neuronal cultures were prepared in duplicate and incubated with hibernate-medium containing Magic Red (1:1000; ImmunoChemistry Technologies, Bloomington, Minn.) at 37° C. for 25 min, followed by the addition of LysoTracker Green DND-26 (50 nM; Thermo Fisher, Waltham, Mass.; see Table 1) for 5 min. The dye-containing medium was then replaced with fresh hibernate-medium, and one group of cultures was incubated at 4° C. for 1, 4 or 16 h, while the other group remained at 37° C. serving as normal controls. The cold-exposed group was subjected to confocal imaging at various temperatures (10° C., room temperature, or 37° C.), while the control group was imaged at either room temperature or 37° C.

These imaging conditions did not influence significantly the measurement of the lysosomal membrane permeability (LMP). Magic Red becomes fluorescent after being cleaved by the lysosomal protease cathepsin B, while DND-26 is an acidotropic probe that accumulates in the acidic lysosomal vesicles. When LMP occurs, Magic Red and DND-26 signals become diffused within the cytoplasm of the affected cells. It was determined that cells have LMP if they contain a single Magic Red-stained particle of diameter >5 μm, which is about the size of the neuronal cell nucleus.

Microtubule Tracing

Cultured neurons or rat retinal explants with or without treatments were fixed with 4% paraformaldehyde, permeabilized and washed with 0.1% Triton X-100 in phosphate buffered saline, and stained by antibodies against TUBB3. TUBB3+ microtubule paths in images of 188.94×188.94 μm$^2$ from human iPSC-derived neuronal cultures and images of 67.48×67.48 μm$^2$ from rat whole-mount retinas were traced with the 'Simple Neurite Tracer' plugin in ImageJ.

Detection of Protein Aggregates

After treatments, cultured neurons were fixed with 4% paraformaldehyde for 10 minutes and then permeabilized and washed with 0.1% Triton X-100 in phosphate buffered saline. Protein aggregates were visualized by a dye that intercalates into the denatured and aggregated proteins and becomes fluorescent (Proteostat aggresome detection kit, Enzo, Farmingdale, N.Y.; see Table 2) (Shen, 2011). For accumulation of protein aggregates on the neuronal microtubules, cells were stained with TUBB3 antibody and the protein aggregate dye, and images (188.94 μm×188.94 μm) were taken. In each image, the number of protein aggregates residing on the microtubules was counted and divided by the total length of the TUBB3+ microtubule paths.

Evaluation on Mouse Kidneys after Cold Storage

Healthy adult C57BL/6J mice under deep anesthetization were first gently perfused by warm 0.9% NaCl solution and hence sacrificed, then the mice were perfused a second time with standard University of Wisconsin Solution for human organ cold storage (UW solution; see Table 1) in control group, or UW solution supplemented with 0.2 μM of the compound having Formula 3/1:200 dilution of protease inhibitor cocktail III in treatment group. To evaluate lipid peroxidation during cold storage, mouse kidneys from the two groups were removed and transferred to 12-well plates containing UW solution or UW solution with the compound having Formula 3/PI, and linoleamide alkyne (from the Click-iT lipid peroxidation imaging kit; Thermo Fisher, see Table 1), set at 20° C. for 30 min. Fresh controls were fixed with 4% paraformaldehyde after this stage, while kidneys in cold-control group and treatment group were then incubated at 4° C. for 24 h. To evaluate tubulin re-polymerization following cold storage, the kidneys were placed at 20° C. for 10 min, rinsed twice with fresh warm UW solution without the compound having Formula 3/PI and then rewarmed in a 37° C. incubator for 30 min. The kidneys were then fixed with 4% paraformaldehyde for 2 h, processed for cryosections, followed manufacturer's instruction to visualized protein/DNA modified by lipid peroxidation, and immunostained for α-tubulin TUBA (see Table 1).

Data Analysis

All data were analyzed for statistical significance using Student's t-test.

DETAILED DESCRIPTION OF THE DRAWINGS

FIGS. 1A to 1G depict species-dependent differences in microtubule stability and transcriptome responses to prolonged cold exposure: TUBB3 (red), polyglutamylated tubulin (poly-E-T; green), or delta2-tubulin (Δ2-T; blue) immunofluorescence in (FIG. 1A) cultured rat primary cortical neurons, (FIG. 1B) human induced pluripotent stem cell-derived neurons (iPSC-neurons), (FIG. 1C) cultured 13-lined ground squirrel (GS) primary cortical neurons, and (FIG. 1D) differentiated GS iPSC-neurons incubated at 4° C. for 0, 4, or 16 hours as indicated. (FIG. 1E) Microtubule lengths from GS cortical primary neurons are unaffected by cold and are quantitatively indistinguishable from GS iPSC-neurons (p>0.05; Student's t-test). Cumulative length plots of manually traced TUBB3-positive microtubules: GS cortical primary neurons (n=5; 37° C. and 4° C.) and GS iPSC-neurons (n=6; 37° C. and 4° C.). Error bars: SEM. (FIG. 1F) Western blot analysis of TUBB3, poly-E-T, and Δ2-T in GS iPSC-neurons and human iPSC-neurons following 4- or 16-h cold exposure with or without TUBB3 overexpression (n=5; Student's t-test;  p<0.01; * p<0.001). (FIG. 1G) Heatmaps of temperature-specific alterations induced by 4° C. incubation for 1 h or 4 h highlighting two distinct categories of expression: genes related to mitochondrial functions, and genes encoding heat shock proteins and protein degradation pathways. Genes exhibiting distinct cold-elicited expression patterns between GS and human neuronal cultures emphasized. Scale: 40 μm.

Figure 2A:
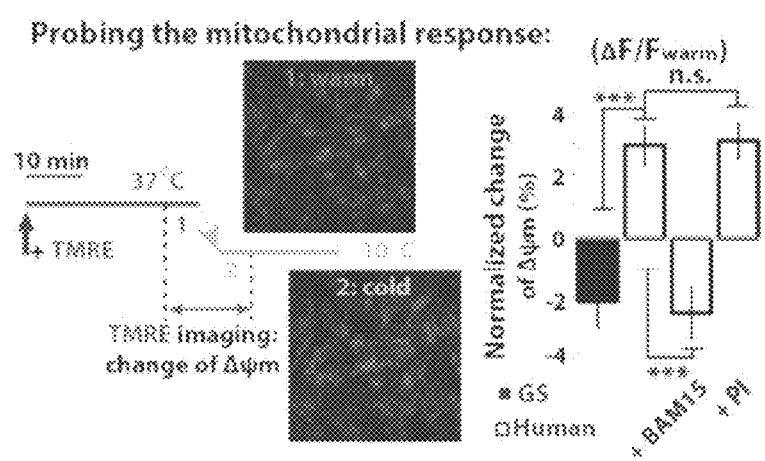
FIGS. 2A to 2F depict cold-induced mitochondrial hyperpolarization, oxidative stress, and lysosomal membrane permeabilization (LMP) in Human iPSC-neurons.
Figure 2B:
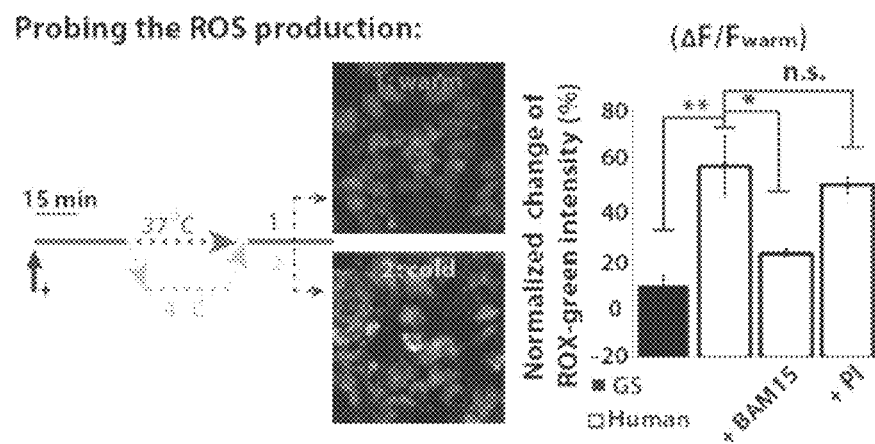
Figure 2C:
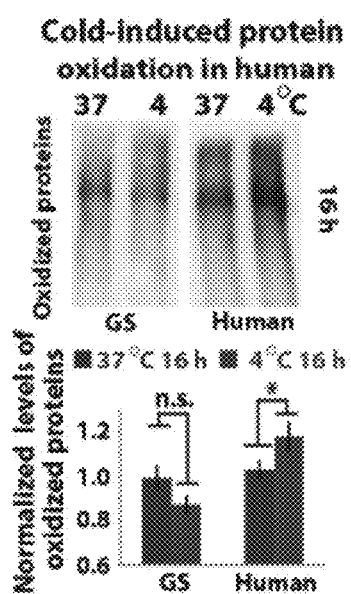
Figure 2D:
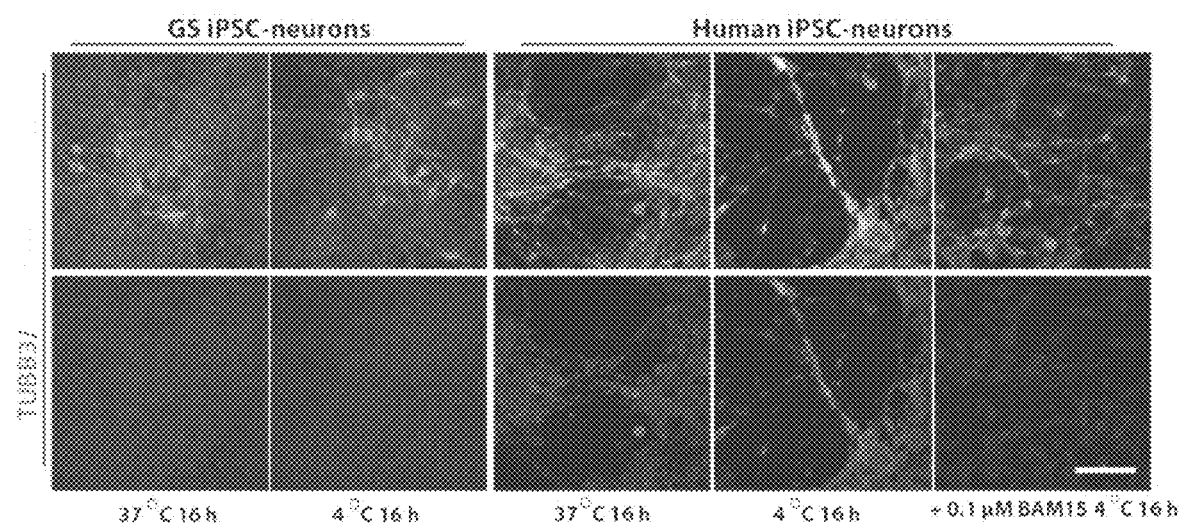
Figure 2E:
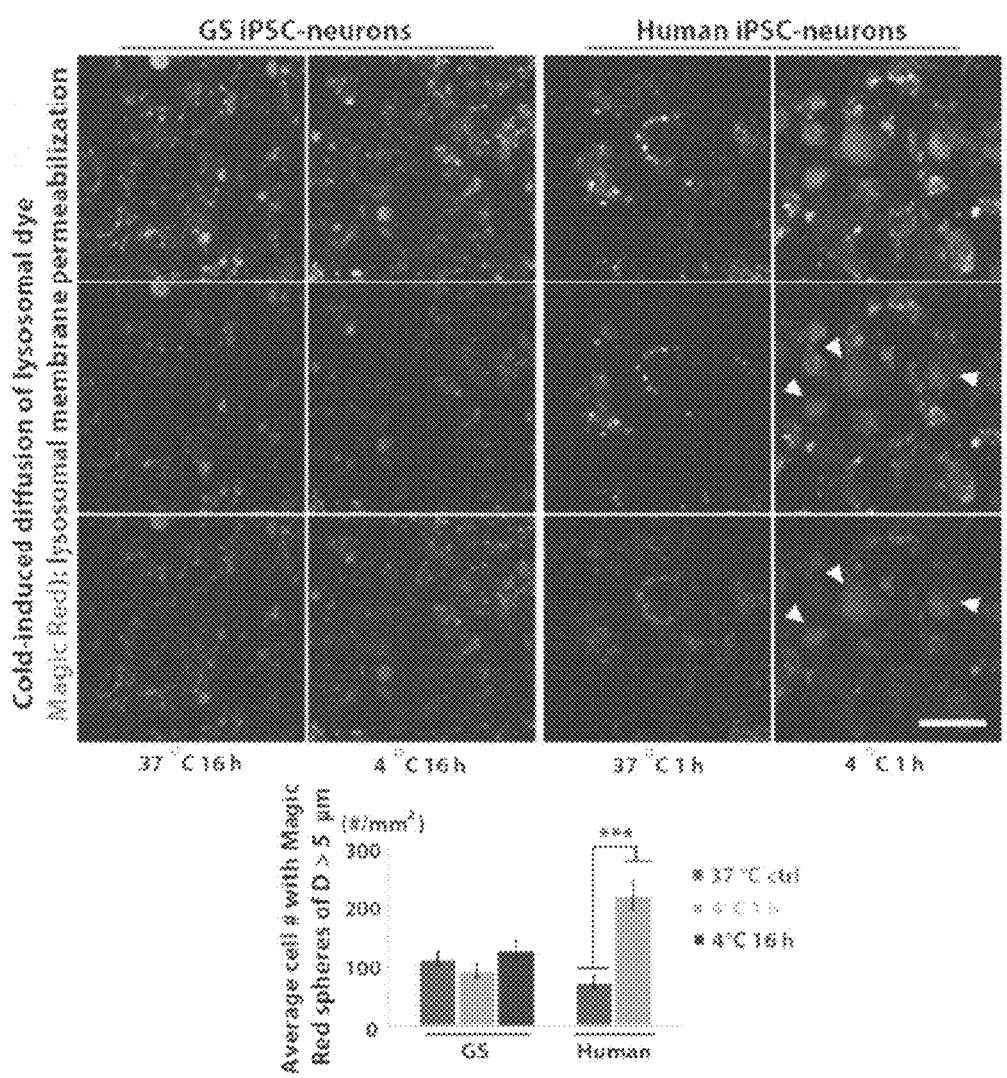
Figure 2F:
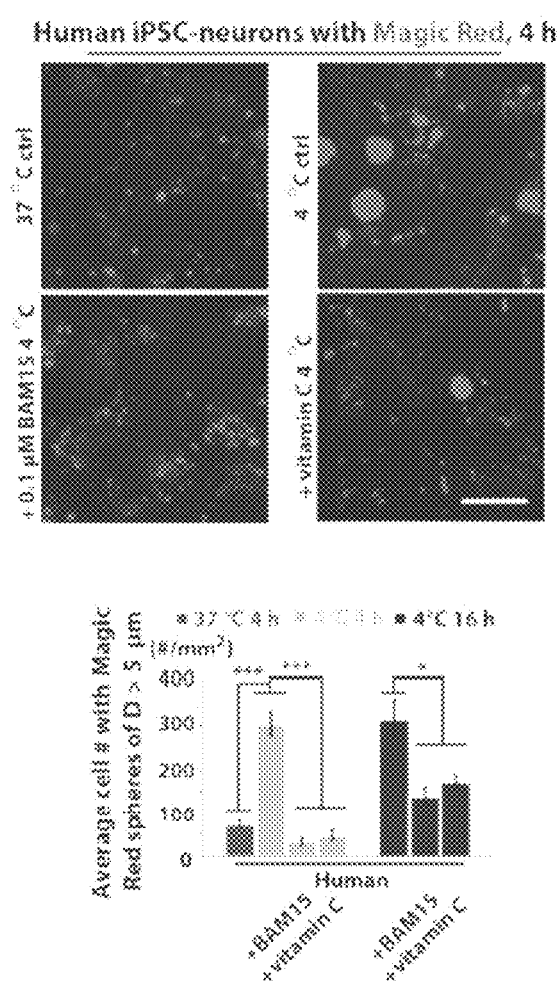

FIGS. 2A to 2F depict cold-induced mitochondrial hyperpolarization, oxidative stress, and lysosomal membrane permeabilization (LMP) in Human iPSC-neurons. (FIG. 2A) Live-cell imaging of mitochondrial membrane potential (Δψ$_m$) with TMRE in cold-exposed GS iPSC-neurons and human iPSC-neurons: treated (compound having Formula 3: a mitochondrial uncoupler or PI: lysosomal protease inhibitors) or untreated (Student's t-test;  p<0.01; * p<0.001). (FIG. 2B) Quantitative image analysis of ROS production (CellROX-green) following 30-min at 4° C. in GS and human iPSC-neurons (Student's t-test; * p<0.05; ** p<0.01). (FIG. 2C) Western blot analysis of oxidized proteins following 16-h at 4° C. (n=5; Student's t-test; * p<0.05). (FIG. 2D) Minimal protein oxidation (green) detected on GS TUBB3+ processes (magenta). Oxidized proteins on residual TUBB3+ microtubules in human neurons were significantly mitigated by the compound having Formula 3. See FIGS. 13A to 13H. (FIG. 2E) Live imaging of lysosomes following 1-h at 4° C. in GS and human iPSC-neurons reveal diffuse cytoplasmic fluorescence (DND-26: green and Magic Red: magenta) in human neurons (arrowheads) indicating LMP. Number of cells containing diffuse Magic Red (Student's t-test; *** p<0.001). (FIG. 2F) Compound having Formula 3 or antioxidant (vitamin C) alleviated LMP in human neurons treated following 4-h at 4° C. Number of cells containing diffuse Magic Red (Student's t-test; * p<0.05; *** p<0.001). See FIGS. 8A to 8C for PQC involvement. Scale: 50 μm (FIG. 2D); 20 μm (FIGS. 2E-2F).

FIGS. 3A to 3D depict morphological protection of human iPSC-neurons by the compound having Formula 3/PI pretreatments against prolonged cold stress. (FIG. 3A) Pretreatment with the compound having Formula 3 (0.1 μM; n=17), PI (1:500; n=24) or a combination of both (n=9) preserved long neurites (poly-E-T: green; TUBB3: red; Δ2-T: blue) of human iPSC-neurons following 4-h incubation at 4° C. See also FIGS. 9A to 9E. (FIG. 3B) Cumulative plots and quantification of TUBB3+ microtubule lengths (compound having Formula 3: n=6; PI: n=5; compound having Formula 3 & PI: n=6; Student's t-test; * p<0.05;  p<0.01; * p<0.001). (FIG. 3C) Western blots and quantification (n=5) confirm the compound having Formula 3 or PI pre-treatment maintain tubulin protein levels in human iPSC-neurons even after 4-h incubation at 4° C. (Student's t-test; ** p<0.01). (FIG. 3D) Proposed model depicting the mechanisms by which the compound having Formula 3 and PI pre-treatments protect human iPSC-neurons from cold stress. Scale bar: 40 μm.

Figure 4A:
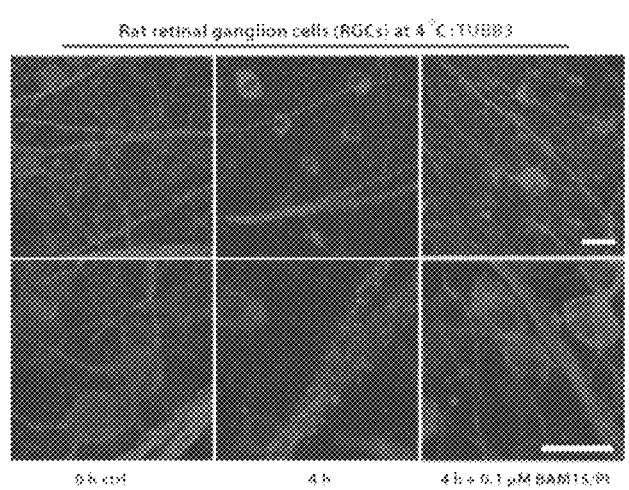
FIGS. 4A to 4E depict protection of rat retinal explants and mouse kidneys by the compound having Formula 3/PI pretreatments against prolonged cold stress.

FIGS. 4A to 4E depict protection of rat retinal explants and mouse kidneys by the compound having Formula 3/PI pretreatments against prolonged cold stress. (FIG. 4A) Microtubule morphology in rat (n=10) retinal ganglion cells (RGCs) immunostained for TUBB3 (red). (FIG. 4B) Cumulative plots of TUBB3+ RGC dendritic lengths in rat retina (n=6; Student's t-test; * p<0.05;  p<0.01). (FIG. 4C) Multielectrode array (MEA) recordings of spontaneous RGC activity following 4° C. for 0 h, 4 h, or 24 h. Treatments applied and corresponding color representation as indicated. Upper-left: Numbers of active RGCs detected by MEA. Upper-right: Average firing rates for detected RGCs. Lower: Distributions of firing rates for detected RGCs. (FIG. 4D) Representative light responses of rat RGCs following 4-h cold exposure either untreated or treated with the compound having Formula 3 (n=5), PI (n=6), or Taxol (n=6). Quantification provided as the percentage of detected RGCs that were light-responsive (Student's t-test;  p<0.01; *** p<0.001). (FIG. 4E) Transverse sections of wild-type mouse kidneys immunostained for α-tubulins (TUBA; green) and DAPI (blue) under conditions indicated. Note: Reduced tubulin signals (arrowheads) in glomeruli and renal tubular epithelium of mouse kidneys stored at 4° C. for 24 h in standard University of Wisconsin Solution. Scale bars: 20 μm (FIG. 4A); (FIG. 4E, upper): 25 μm; (FIG. 4E, middle/lower): 5 μm. See FIGS. 10A and 10B.

Figure 5A:
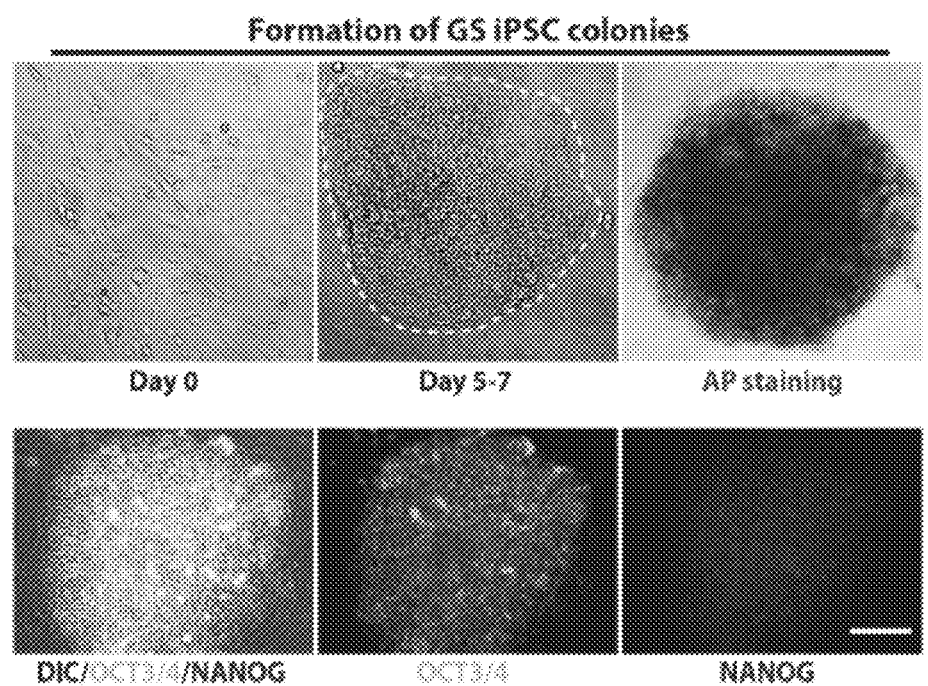
FIGS. 5A to 5C depict pluripotency characterization of ground squirrel induced pluripotent stem cells (GS iPSCs)
Figure 5B:
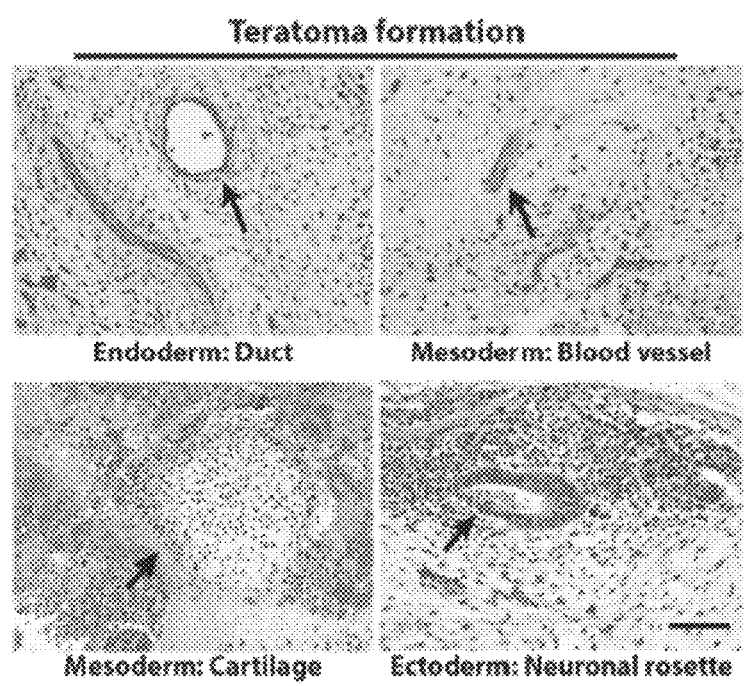
Figure 5C:
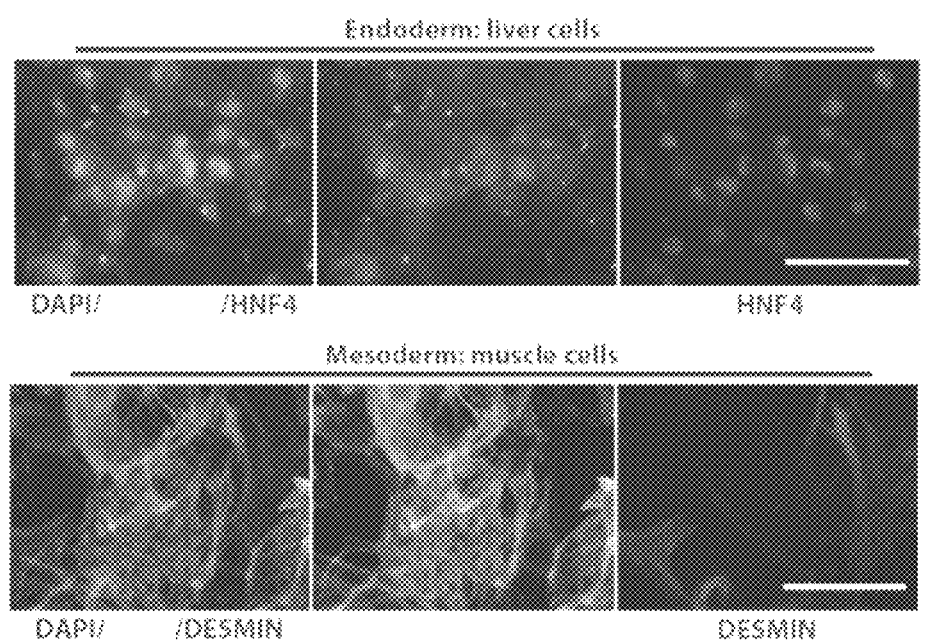

FIGS. 5A to 5C depict pluripotency characterization of ground squirrel induced pluripotent stem cells (GS iPSCs). (FIG. 5A) Formation and characterization of GS iPSC colonies (see METHODS). GS iPSC colonies stained positive for pluripotency markers: alkaline phosphatase (AP), OCT3/4 (green), and NANOG (red). (FIG. 5B) Hematoxylin and eosin stained cross-sections of GS iPSC teratomas (see METHODS) demonstrate 3-germ layer differentiation capability (arrows). (FIG. 5C) (Left panel) GS iPSCs differentiated into liver cells, a signature cell type of the endoderm, and stained by antibodies against liver cell markers: ALBUMIN (green), HFN4 (red) and the cell nuclear dye DAPI (blue). (Right Panel) GS iPSCs were differentiated into muscle cells, a signature cell type of the mesoderm, and stained by antibodies against muscle cell markers: Troponin T (TNNT, green), DESMIN (red) and DAPI (blue). Scale bars: 150 μm (FIGS. 5A and 5B); 50 μm (FIG. 5C).

Figure 6A:
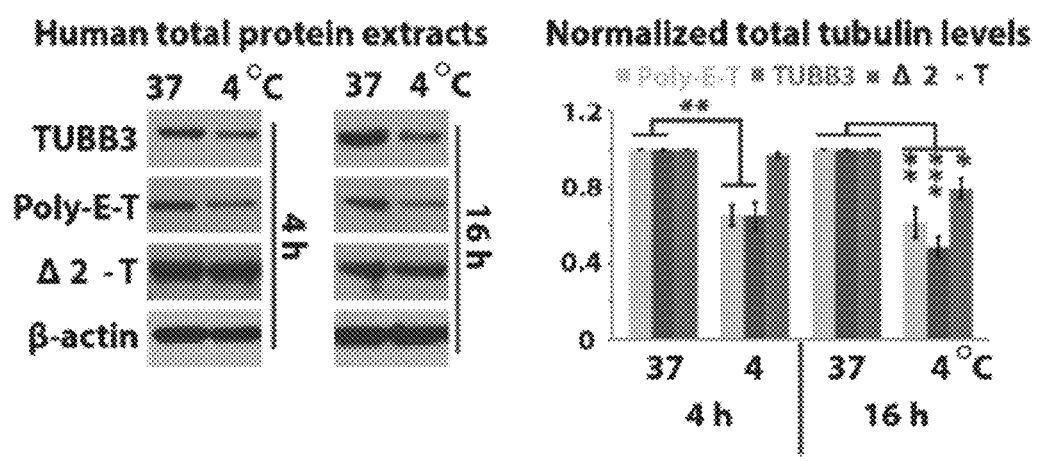
FIGS. 6A and 6B depict the effects of TUBB3 overexpression and Taxol on protecting neuronal microtubules of human iPSC-neurons against cold stress.
Figure 6B:
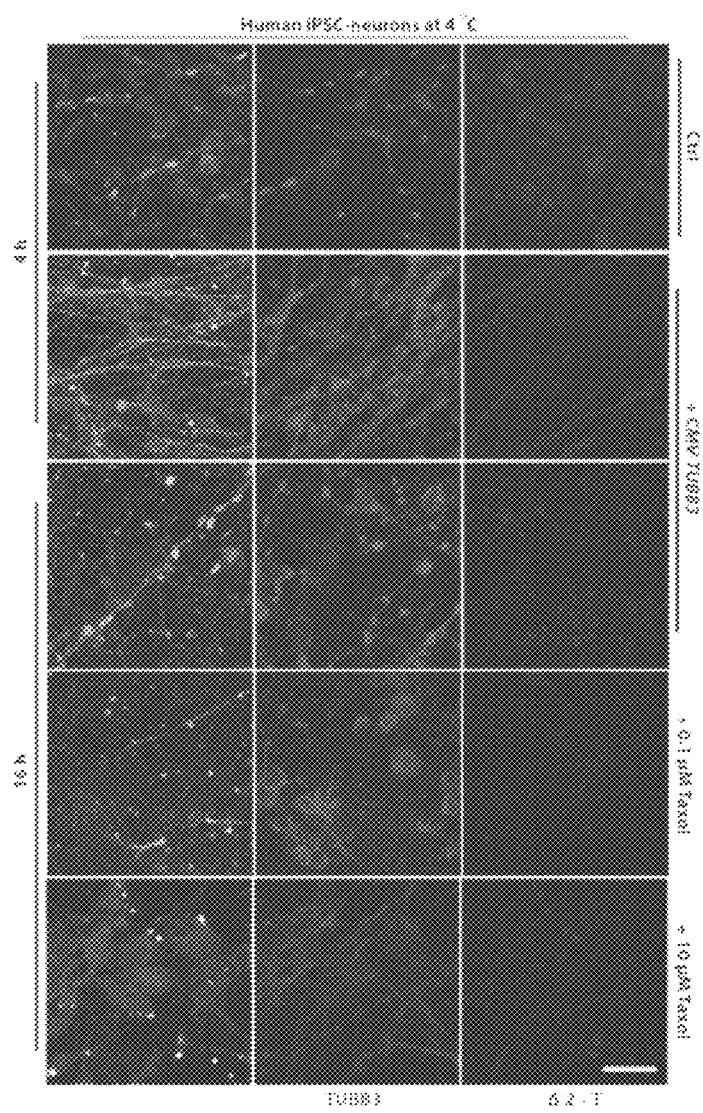

FIGS. 6A and 6B depict the effects of TUBB3 overexpression and Taxol on protecting neuronal microtubules of human iPSC-neurons against cold stress. (FIG. 6A) Western blots and quantification of total TUBB3, poly-E-T and Δ2-T proteins in human iPSC-neurons following 4- or 16-h cold exposure with or without TUBB3 overexpression (n=5; Student's t-test; * p<0.05;  p<0.01; * p<0.001). (FIG. 6B) Immunofluorescence of TUBB3 (red), poly-E-T (green), or Δ2-T (blue) in human iPSC-neurons incubated at 4° C. for 4 or 16 h. Note: Overexpression of TUBB3 improved microtubule morphology only in the 4-h cold-stressed group; Taxol is a known drug that binds and stabilizes microtubules. Low dose Taxol (0.1 μM) did not protect human iPSC-neuronal microtubules following 16-h cold exposure. Scale bar: 40 μm.

Figure 7A:
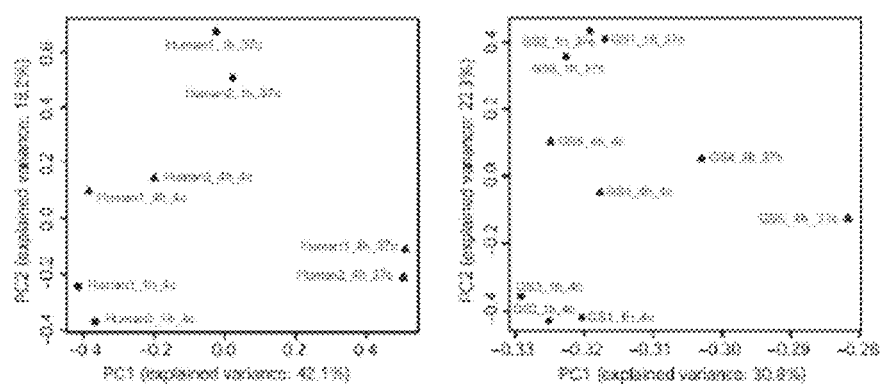
Figure 7B:
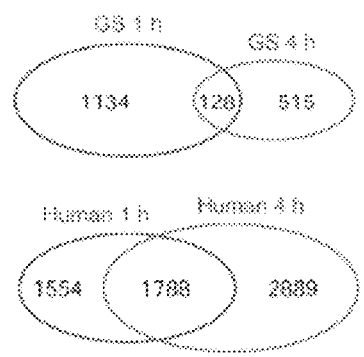
Figure 7C:
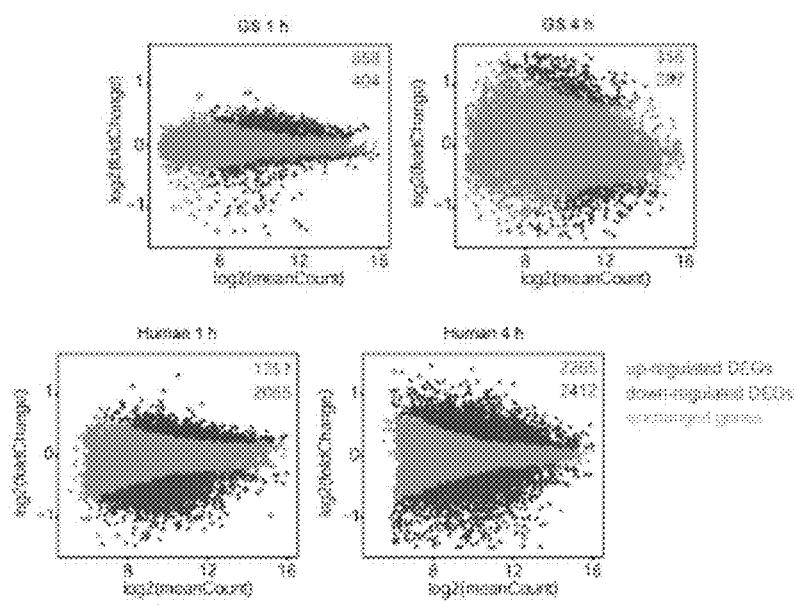
Figure 7D:
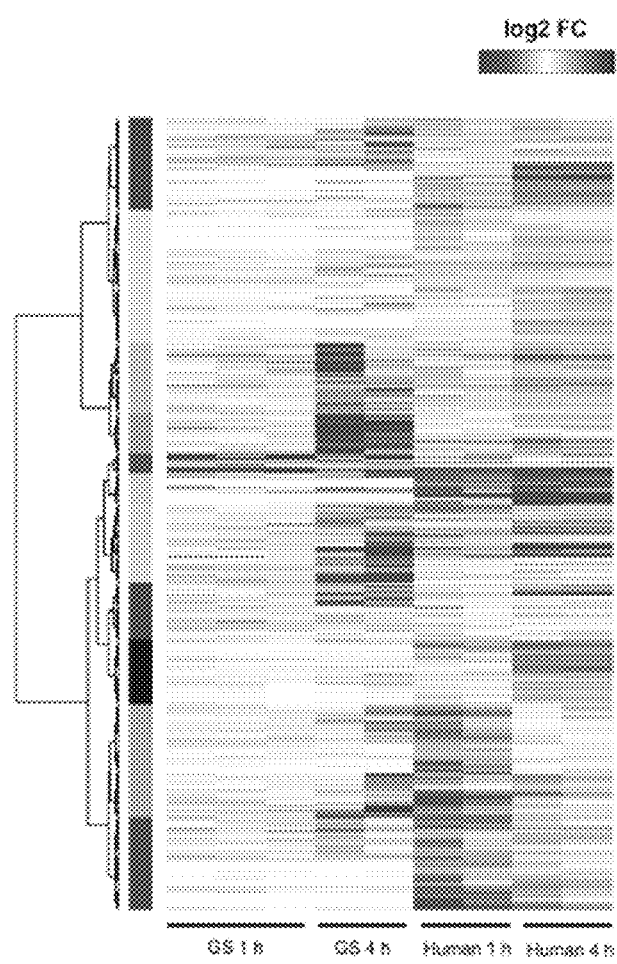
Figure 7E:
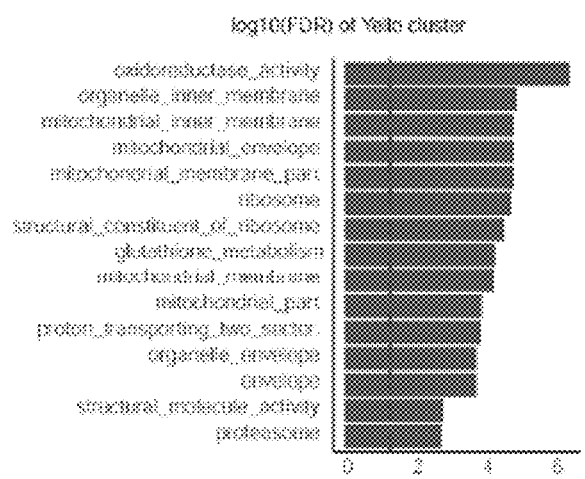
Figure 7F:
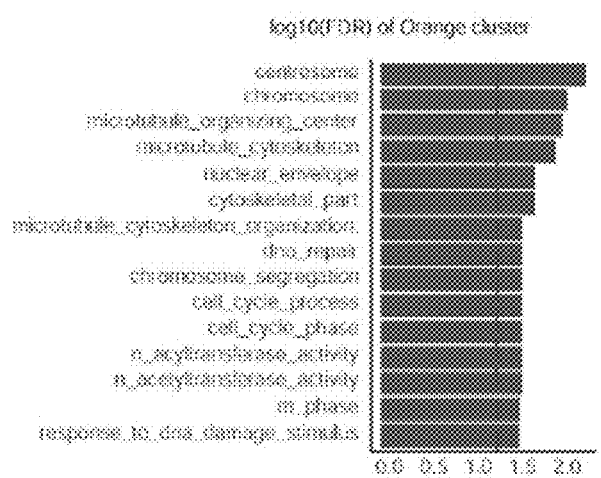

FIGS. 7A to 7G depict bioinformatics analyses on GS and human iPSC-neurons. (FIG. 7A) Factorial map of the principal-component analysis (PCA) of scaled mRNA RPKM values. Top variant mRNAs were used. The proportion of the variance explained by the principal components is indicated in parentheses. (FIG. 7B) Venn plot showing comparisons of differentially expressed genes (DEGs). (FIG. 7C) M-A plots showing changes in gene expression in GS and human iPSC-neurons. M: $\log_2$ mRNA fold change, A: $\log_2$ mean count per-million (CPM). Red dots: significant up-regulated genes with adjusted P<0.05; blue dots: significant downregulated genes with adjusted P<0.05. Colored numbers in upper right correspond to the number of DEGs (upregulated: red; downregulated: blue). (FIG. 7D) Clustering analysis of DEG orthologs with similar expression fold change. Sub-clusters are colored in red (785 genes), yellow (1150), grey (598), green (359), purple (167), pink (278), sky-blue (682), blue (499), black (549), orange (971), and claret (785) (top to bottom). $\log_2$ of DEGs fold change matrix was used. (FIG. 7E) GO terms or KEGG pathway analysis on DEGs in yellow sub-cluster from (FIG. 7D). (FIG. 7F) GO terms or KEGG pathway analysis on DEGs in orange sub-cluster from (FIG. 7D). (FIG. 7G) An example of TUBB3 predicted acetylation sites. TUBB3 protein sequences from human, mouse, rat, and ground squirrel were aligned. Identical amino acids in the same corresponding positions of multiple alignments are colored in red.

Figure 8A:
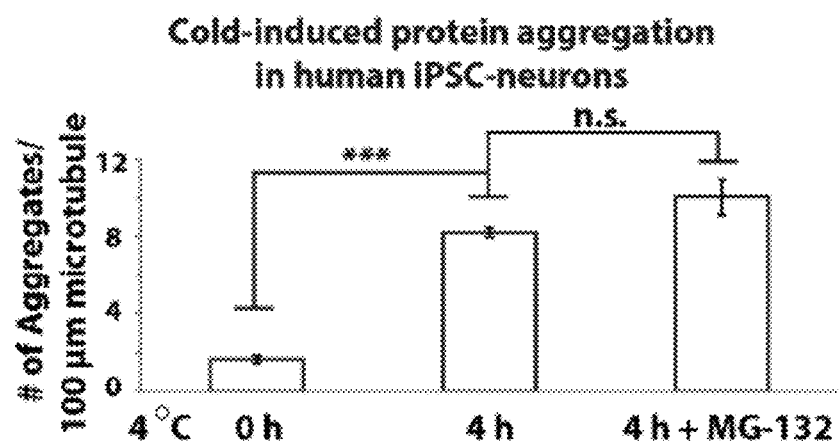
FIGS. 8A to 8C depict association of protein oxidation and aggregation on the microtubules of cold-stressed human iPSC-neurons.
Figure 8B:
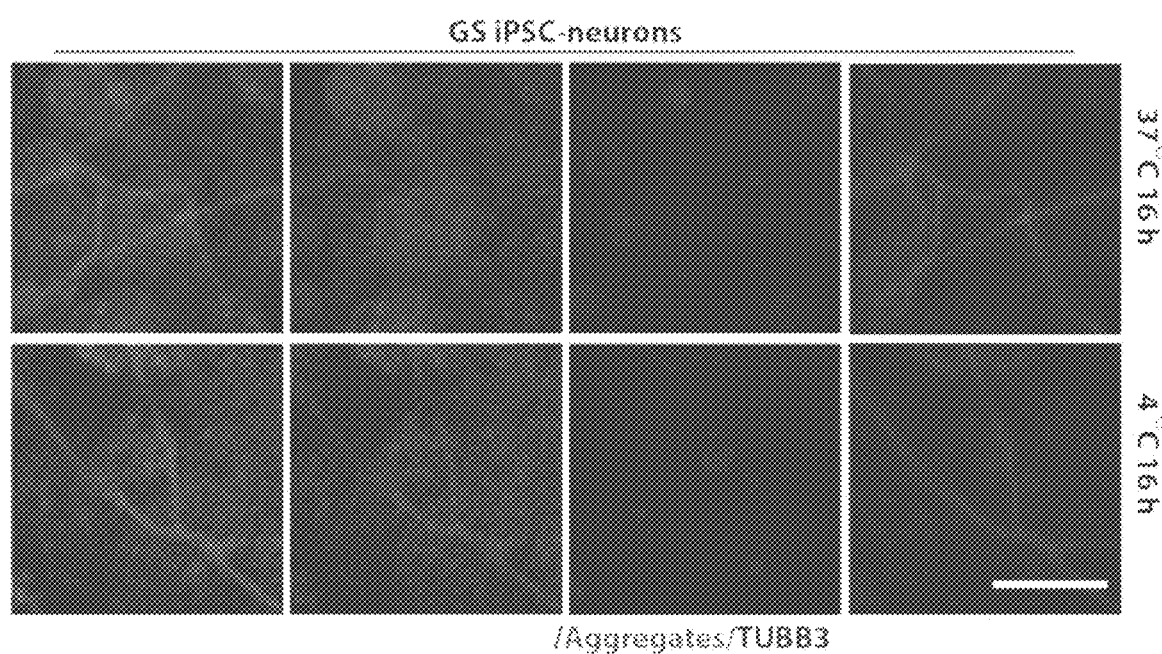
Figure 8C:
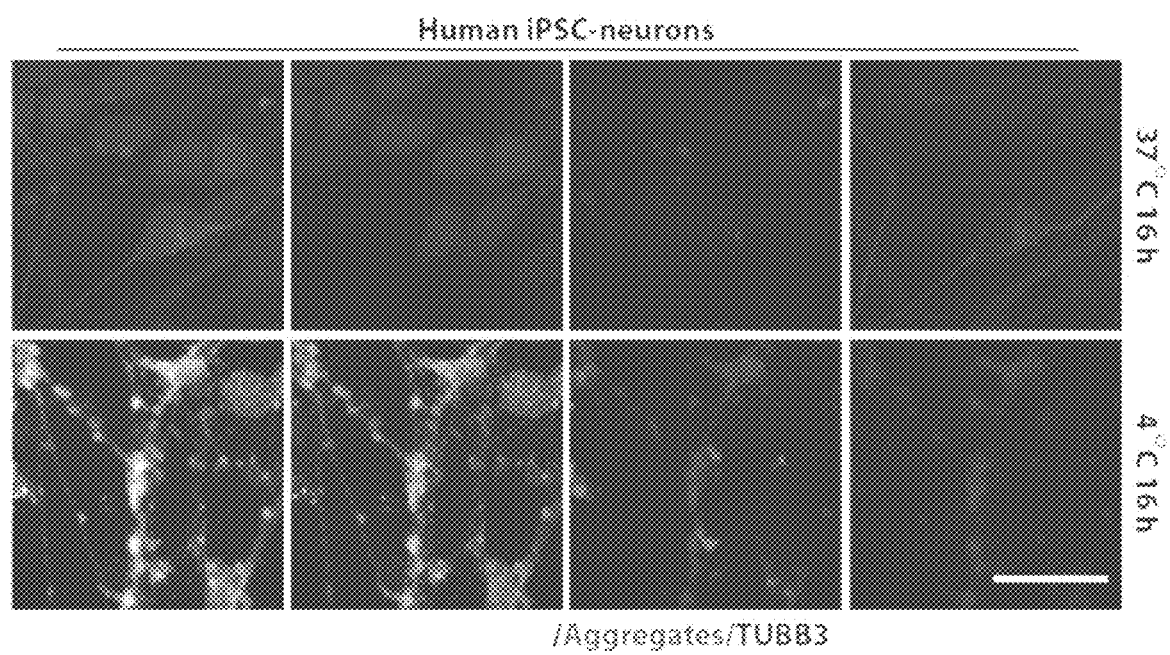

FIGS. 8A to 8C depict association of protein oxidation and aggregation on the microtubules of cold-stressed human iPSC-neurons. (FIG. 8A) In human iPSC-neurons, incubation at 4° C. for 4 h was sufficient to cause accumulation of protein aggregates along the microtubule processes, while pre-incubation with MG-132, a proteasome-specific inhibitor known to induce cellular protein aggregate formation, did not show any further increase in aggregation (Student's t-test; n.s. not significant; *** p<0.001). This result is consistent with our finding that in human iPSC-neurons vasolin-containing proteins (VCPs) and chaperone proteins (HSPs) that regulate ubiquitin-mediated protein degradation were downregulated at 4° C., compromising the delivery of damaged proteins via VCP to proteasomes. (FIG. 8B) Immunofluorescence of TUBB3 (blue), oxidized proteins (green) and a protein aggregate-binding dye (red; see METHODS) in GS iPSC-neurons. (FIG. 8C) Immunofluorescence of TUBB3 (blue), oxidized proteins (green), and a protein aggregate-binding dye (red) in human iPSC-neurons. Scale bars: 20 μm.

Figure 9A:
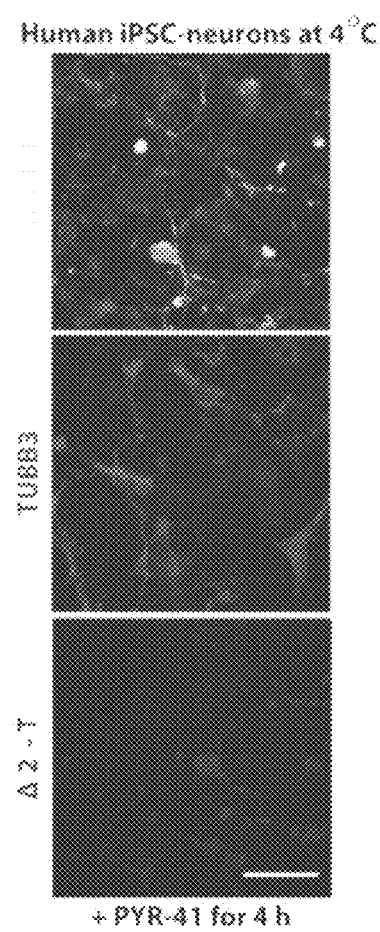
FIGS. 9A to 9E depict evaluation of key components of the PQC system in cold-stressed human iPSC-neurons.
Figure 9B:
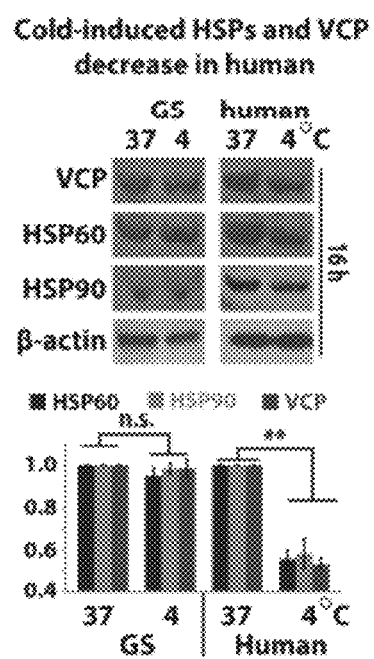
Figure 9C:
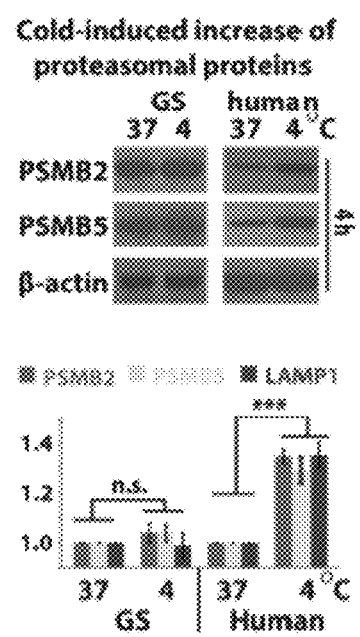
Figure 9D:
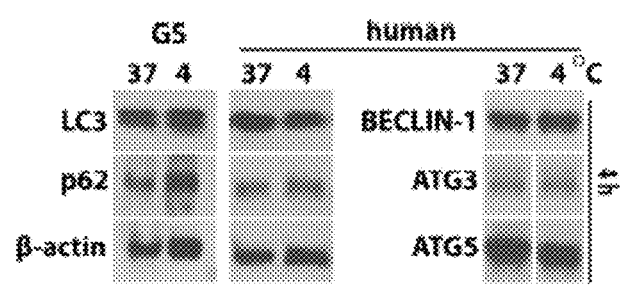
Figure 9E:
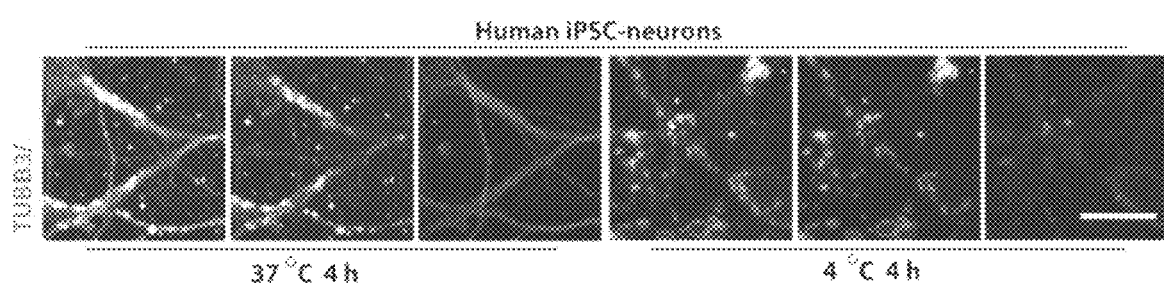

FIGS. 9A to 9E depict evaluation of key components of the PQC system in cold-stressed human iPSC-neurons. (FIG. 9A) Pre-treatment with PYR-41, an inhibitor of protein ubiquitination did not improve microtubule morphology (poly-E-T: green; TUBB3: red; Δ2-T: blue) during 4-h incubation at 4° C. (FIG. 9B) Western blots and quantification of vasolin-containing protein (VCP) and molecular chaperones (HSP60 and HSP90) in human and GS iPSC-neurons after 16-h incubation at 4° C. (n=5; Student's t-test;  p<0.01; n.s. p>0.05, not significant). (FIG. 9C) Western blots and quantification of proteasomal subunits PSMB2 and PSMB5 in human and GS iPSC-neurons after 4-h incubation at 4° C. (n=5; Student's t-test; n.s. not significant; * p<0.001). (FIG. 9D) Protein levels of key autophagosome components remain unchanged in GS and human iPSC-neurons after 4-h cold exposure. (FIG. 9E) Immunofluorescence of TUBB3 (magenta) and LAMP1 (green; lysosomal marker) show evidence of lysosomal localization on microtubule processes of human iPSC-neurons. Scale bars: 30 μm (FIG. 9A); 20 μm (FIG. 9E).

Figure 10A:
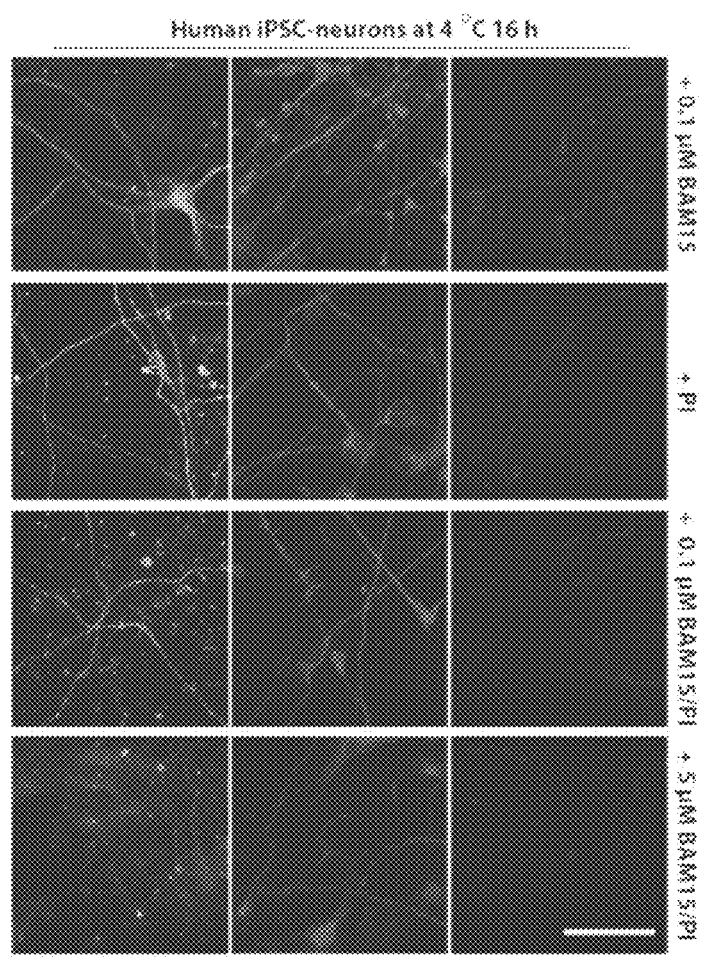
FIGS. 10A and 10B depict partial rescue of human iPSC-neuronal microtubules by the compound having Formula 3/PI from overnight cold stress.
Figure 10B:
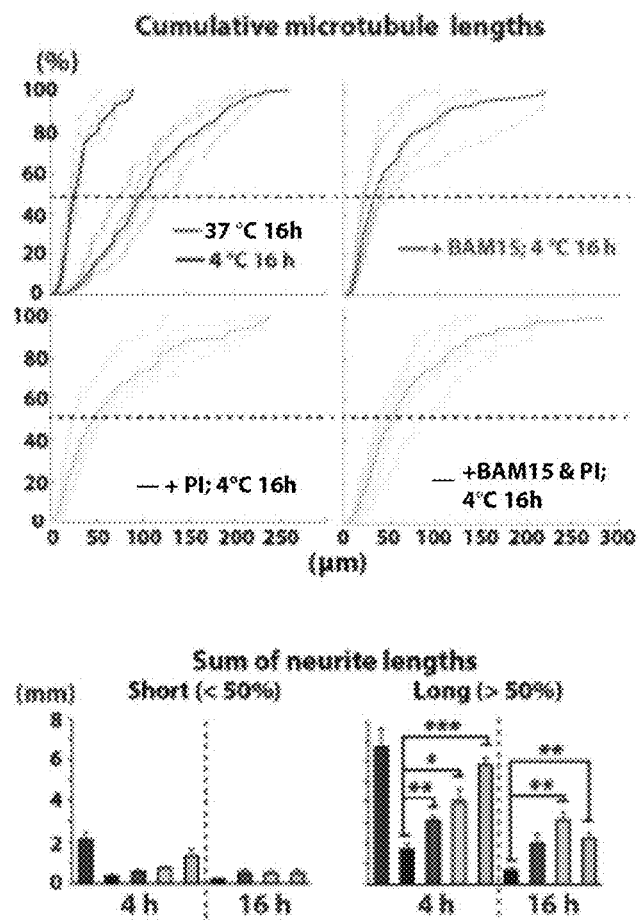

FIGS. 10A and 10B depict partial rescue of human iPSC-neuronal microtubules by the compound having Formula 3/PI from overnight cold stress. (FIG. 10A) Immunofluorescence of TUBB3 (red), poly-E-T (green), or Δ2-T (blue) in human iPSC-neurons incubated at 4° C. for 16 h. Note: High concentration of the compound having Formula 3 (5 µM; n=5) exhibited poor microtubule morphology. (FIG. 10-B) Cumulative plots and quantification of the lengths of TUBB3+ microtubules of human iPSC-neurons (0.1 µM of the compound having Formula 3: n=6; 1:500 PI: n=5; 0.1 µM of the compound having Formula 3 & 1:500 PI: n=6) following 4- and 16-h cold stress (Student's t-test; * p<0.05;  p<0.01; * p<0.001). Scale bar: 40 µm.

Figure 11A:
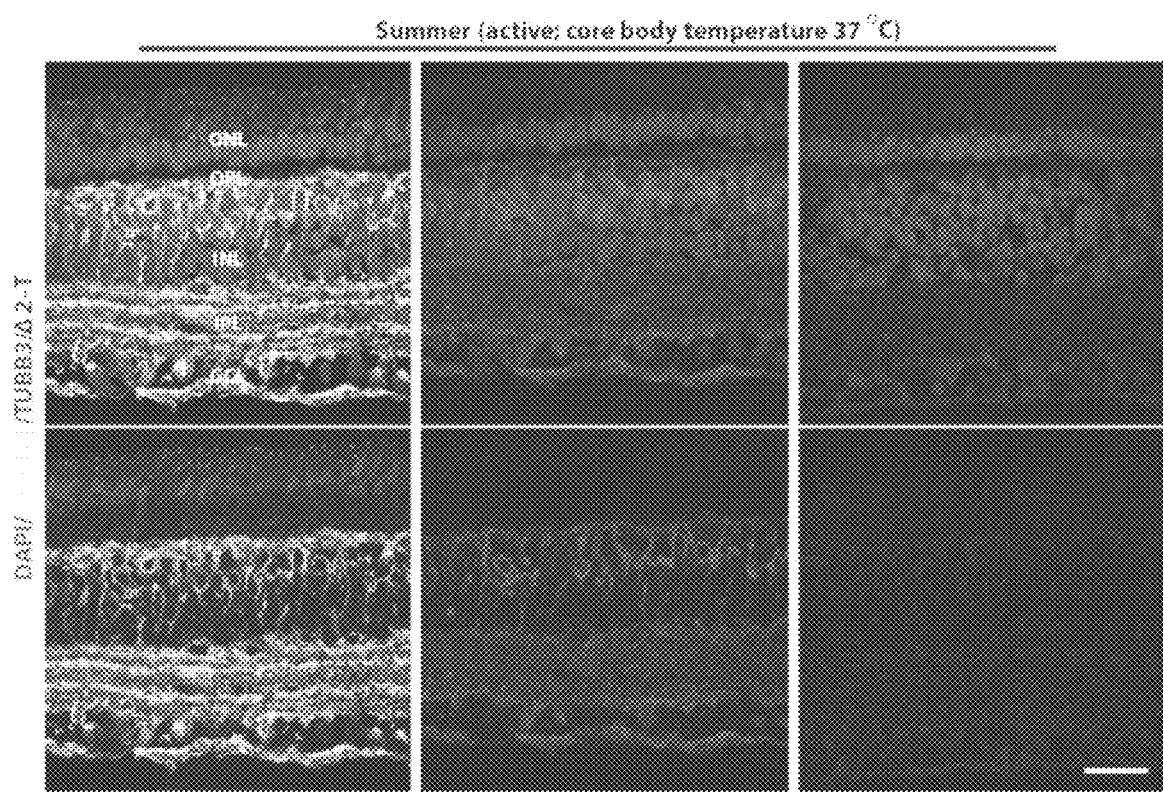
FIGS. 11A and 11B depict GS retina neuronal microtubule morphology barely changed during hibernation.
Figure 11B:
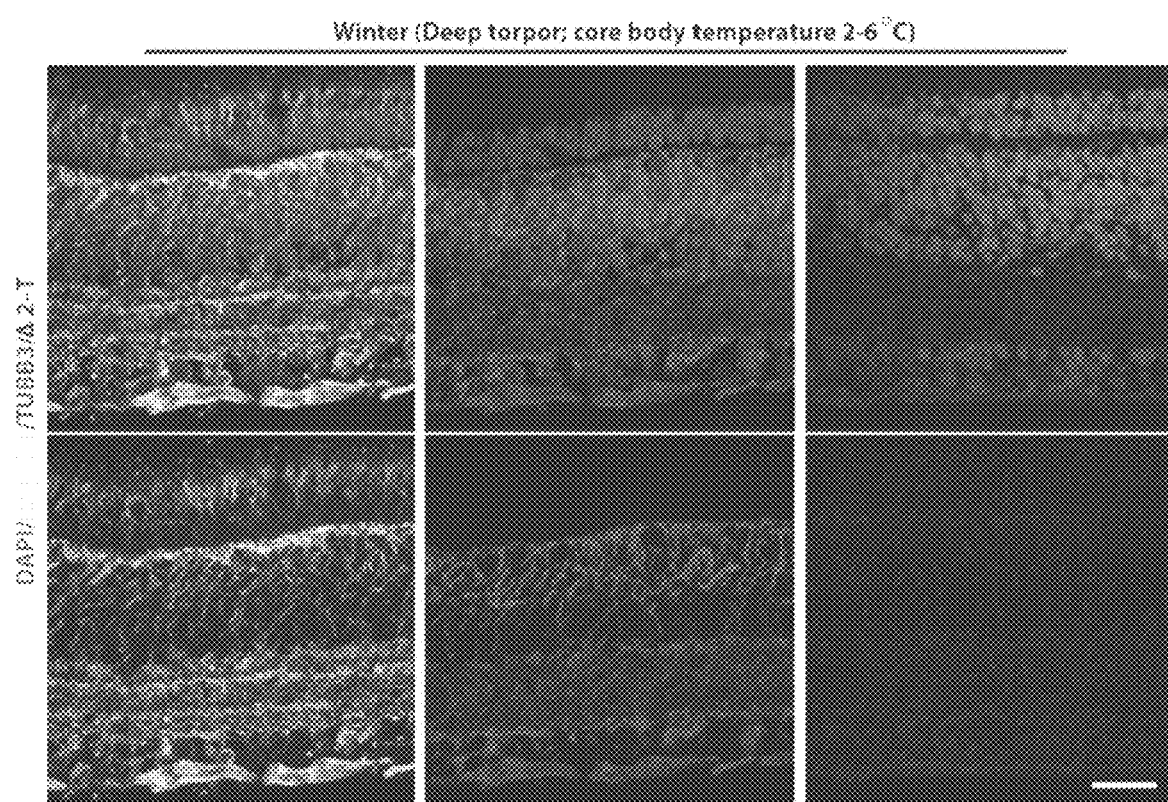

FIGS. 11A and 11B. GS retina neuronal microtubule morphology barely changed during hibernation. (FIG. 11A) Immunofluorescence of TUBB3 (red), poly-E-T (green), or Δ2-T (blue) on retinal sections from summer active GS. (FIG. 11B) Immunofluorescence of TUBB3 (red), poly-E-T (green), or Δ2-T (blue) on retinal sections from GS under deep torpor during the winter hibernating season. The gross anatomical structures of the retinal sections were not noticeably different between active and hibernating GS. Cell nuclei were stained with DAPI (magenta). ONL—outer nuclear layer; OPL—outer plexiform layer; INL—inner nuclear layer; IPL—inner plexiform layer; GCL—ganglion cell layer. Scale bar: 50 µm.

Figure 12:
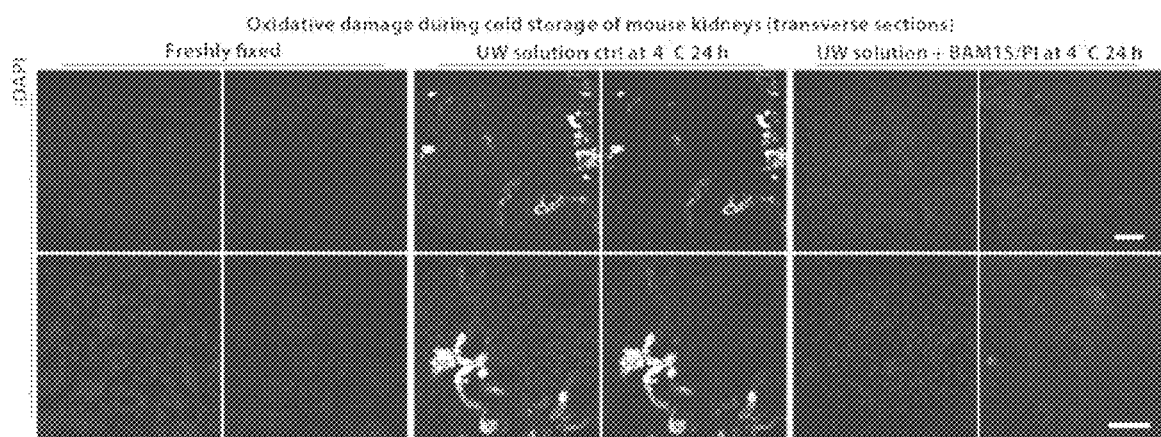
FIG. 12 depicts inhibiting damages caused by lipid peroxidation by the compound having Formula 3/PI during cold storage of mouse kidneys.

FIG. 12 depicts inhibiting damages caused by lipid peroxidation by the compound having Formula 3/PI during cold storage of mouse kidneys. Kidneys from healthy wild-type mice were sectioned and visualized for proteins modified by lipid peroxidation (green; see METHODS). Scale bars: 50 µm.

FIGS. 13A to 13H depict alignment of predicted protein sequences of tubulin genes identified in the transcriptome of GS iPSC-neurons. No species-specific fragments were found in the predicted tubulin protein sequences among human, mouse, rat and GS.

DISCUSSION

Figure 1B:
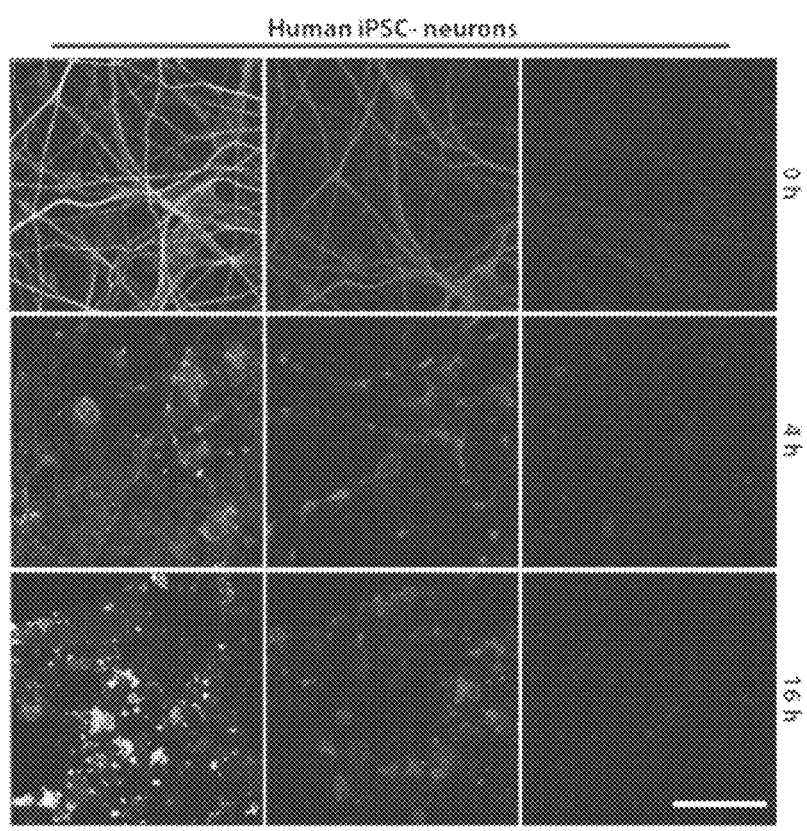
Figure 1C:
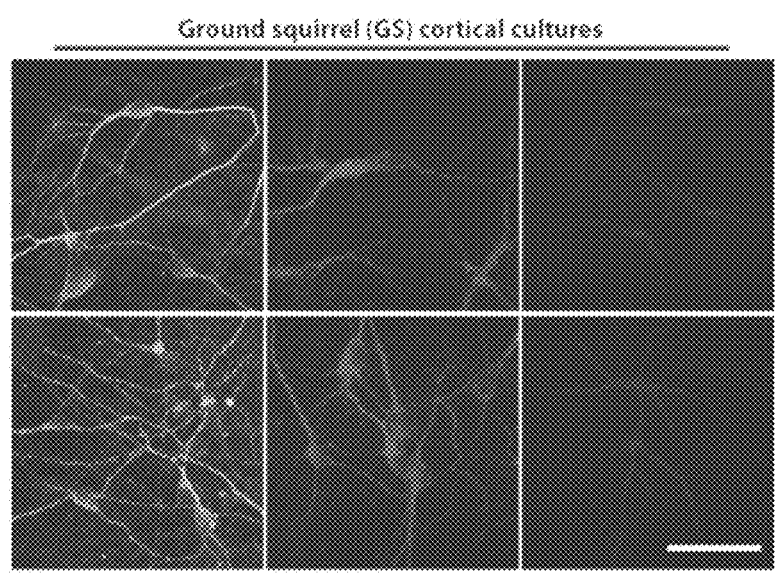
Figure 1D:
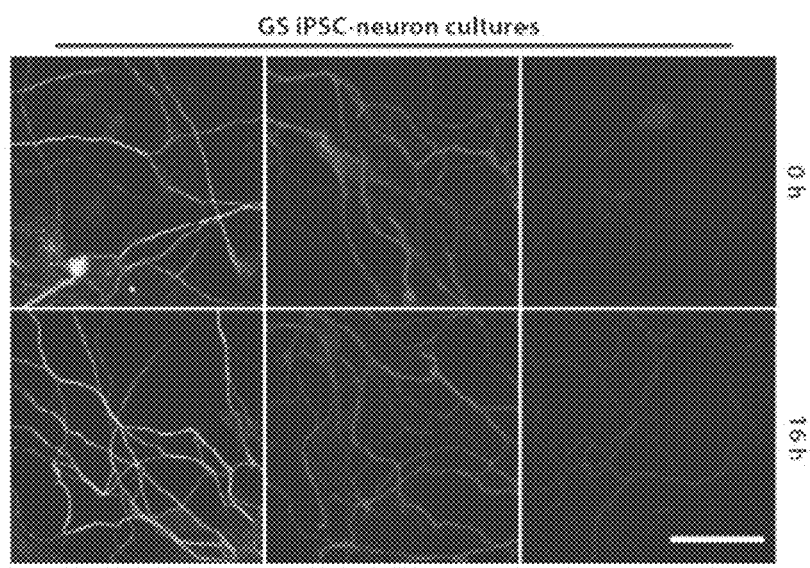
Figure 1E:
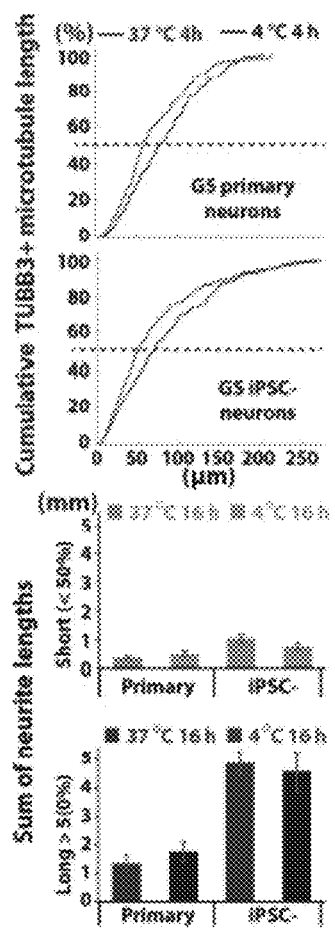

The inventors of the present invention (hereinafter "the inventors") compared microtubule morphology in cultured cortical neurons from neonatal GSs and rats (a non-hibernator) at 4° C. using antibodies against the neuron-specific β-tubulin isotype-III (TUBB3) and two α-tubulin isotypes that are enriched in neurons (Δ2-T, Poly-E-T). Four hours at 4° C. induced microtubule fragmentation in rat neurons, while after 16-h, most microtubules disappeared, leaving abnormal tubulin aggregates (FIG. 1A). Furthermore, human neurons (derived from iPSCs) exhibited similar cold-induced microtubule instability (FIG. 1B). In stark contrast, GS neurons+ showed no signs of deterioration even at 16 h of cold exposure and thus appear to contain cold-resistant microtubules (FIG. 1C).

Figure 1F:
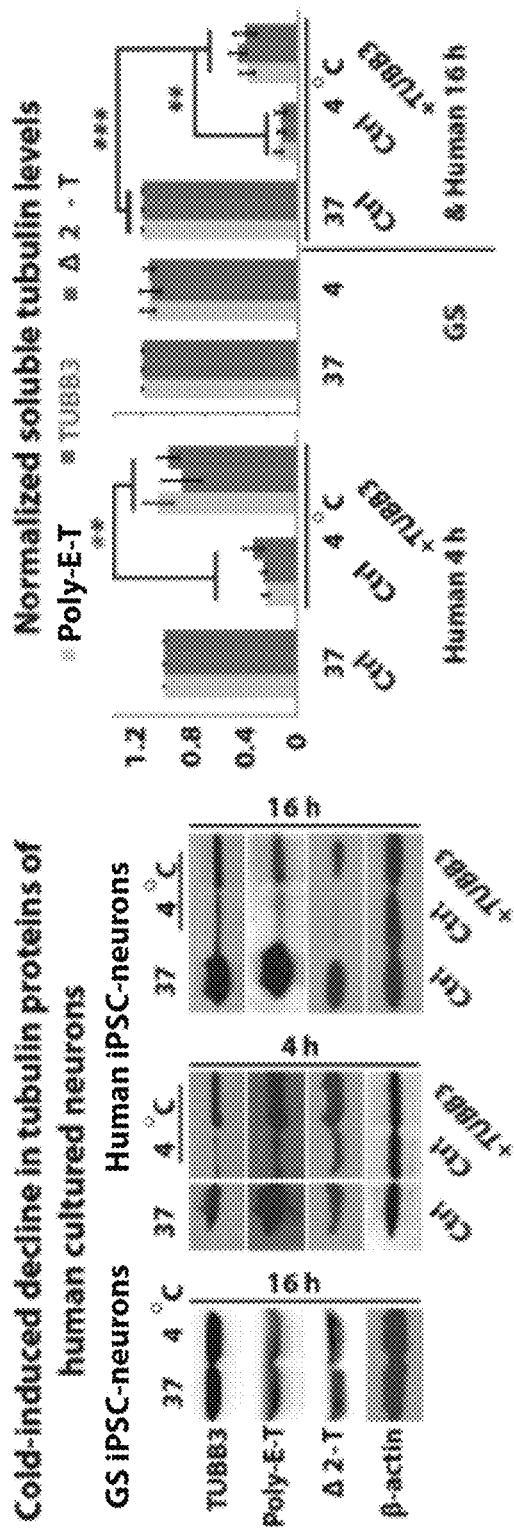

To overcome the limited accessibility of primary cultures of GS neurons and facilitate mechanistic studies of microtubule cold resistance in vitro, the inventors established GS iPSC lines from neonatal GS cortex and validated their pluripotency (FIGS. 5A to 5C). As with GS cortical primary neurons, microtubules of GS iPSC-neurons showed little difference between 37° C. and 4° C. incubation for 16 h (FIGS. 1D and 1E), suggesting that GS iPSC-neurons retain this endogenous cold-resistance. Consistently, protein levels of TUBB3, poly-E-T, and Δ2-T remained unchanged following 16-h incubation at 4° C., whereas in human iPSC-neurons following 4 h at 4° C., tubulin protein levels were significantly reduced (FIG. 1F and FIG. 6A).

To test whether cold-induced microtubule destabilization results from impaired tubulin synthesis, TUBB3 in human iPSC-neurons were overexpressed. Such overexpression was transiently effective, preserving levels of all three proteins (TUBB3, poly-E-T, and Δ2-T) and improving microtubule stability during 4-h cold exposure (FIG. 1F and FIG. 6B), likely by recruiting poly-E-T and Δ2-T to form more stable polymers. However, this rescue effect did not extend to the 16-h group (FIG. 6B), suggesting that it is ultimately outpaced by cellular activities related to microtubule degradation.

Figure 1G:
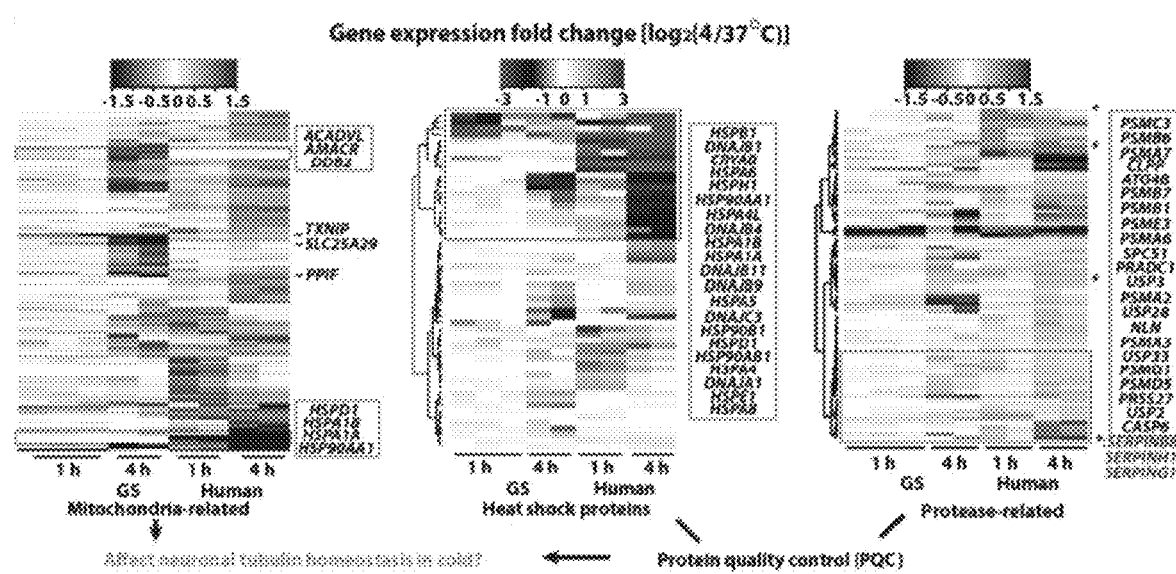

Multiple mechanisms could contribute to differential microtubule stability between GS and human iPSC-neurons. The inventors probed common mechanisms, finding: 1) isotypes or amino acid sequences of tubulins were analogous (FIGS. 7A to 7G and 8A to 8C); 2) common neuron-enriched post translational modifications were similar (poly-E-T and Δ2-T; FIGS. 1A to 1G); and 3) microtubule-stabilizing MAP (i.e., MAP6) was not differentially regulated by temperature in human vs. GS iPSC-neurons. However, by examining profiles of cold-triggered differentially expressed genes (DEGs) and clustering them according to their putative functions and pathways (FIGS. 7A to 7G), two major gene clusters were identified: 1) mitochondria-related genes and 2) genes participating in protein quality control (PQC), including protease-related genes (FIG. 1G). These differentially affected pathways prompted us to investigate the mitochondrial and PQC responses to cold in live cells.

To examine whether mitochondria in human and GS iPSC-neurons respond differently to cold exposure, mitochondrial membrane potential ($\Delta\psi_m$) changes were monitored using tetramethylrhodamine ethyl ester (TMRE) fluorescence in live cultured neurons. In human iPSC-neurons following temperature decrease from 37° C. to 10° C., a 3% increase in TMRE fluorescence intensity was observed, indicating a hyperpolarization of $\Delta\psi_m$ (FIG. 2A). In contrast, under the same conditions GS iPSC-neurons exhibited a 2% decrease, indicating depolarization (FIG. 2A). Due to the steep nonlinear relationship between $\Delta\psi_m$ and ROS production for mitochondria near normal ranges of $\Delta\psi_m$ (Starkov, 2003), these seemingly modest changes in TMRE signal will therefore correspond to significant alterations in reactive oxygen species (ROS) production. Indeed, following 30-min cold exposure with CeliROX Green, significantly higher cold-induced ROS production in human than GS iPSC-neurons was observed (FIG. 2B). Interestingly, in isolated mouse cortical mitochondria, mild hypothermia has a similar effect, suggesting non-hibernators share a common response to cold (Ali, 2010). Moreover, when the mitochondrial hyperpolarization was reversed by addition of the uncoupler compound having Formula 3, a significant decrease in ROS production to levels comparable to GS iPSC-neurons in the cold was observed (FIG. 2B).

ROS has been reported to oxidize and destabilize microtubules (Wilson, 2015). Consistently, it was found that levels of oxidized proteins increased in human but not GS iPSC-neurons (FIG. 2C). Oxidized proteins are subject to protein-protein cross-linkages resulting in aggregate formation (Grune, 1997; Gregersen, 2010). Indeed, immunolabeling of oxidized proteins revealed aggregates along residual microtubules after cold exposure in human but not GS iPSC-neurons (FIG. 2D and FIGS. 8A to 8C). Furthermore, the compound having Formula 3 prevented accumulation of oxidized proteins along microtubules (FIG. 2D). Therefore, hibernators may have evolved to evade oxidative stress by minimizing mitochondrial hyperpolarization. Consistently, in winter, the maximum $\Delta\psi_m$, of GS brain mitochondria during torpor (5° C.) is slightly more depolarized compared to that during inter-bout arousal (37° C.) (Ballinger, 2017). Intriguingly, in both winter states $\Delta\psi_m$, is more hyperpolarized than that in spring, suggesting possible seasonal preconditioning. Mechanistically, free fatty acids (Dedukhova, 1991; Skulachev, 1991) produced by augmented lipid metabolism during hibernation or intrinsic uncoupling protein expression (Staples, 2016) likely contribute to higher proton leak, thus conferring protection against cold-induced ROS damage.

An over-abundance of oxidative proteins normally engages the ubiquitin-proteasome dependent PQC system for removal (Zhang, 2014; Goldberg, 2003), with lysosomes providing an alternative pathway (Iwata, 2005; Dunlop, 2009; Lee, 2012). However, in cold-treated human iPSC-neurons PQC dysregulation was observed (FIG. 1G and FIGS. 9B and 9C), and evidence of compromised lysosomal integrity (i.e., lysosomal membrane permeability, LMP) was surprisingly found. In GS and human iPSC-neurons at 37° C., Magic Red and DND-26 labeled discrete puncta, indicating lysosomal vesicles, but became more diffuse in cold-exposed human neurons (FIG. 2E; arrowheads), typical signs of LMP and an acidified cytosolic environment. Thus, leaked proteases from lysosomes are poised to inadvertently digest nearby cytosolic proteins such as adjacent microtubules (FIG. 9E).

Lysosomal dysfunction has been reported to impair microtubule structure (Fukuda, 2006). Conversely, both destabilized microtubules and enhanced ROS have been shown to trigger LMP (Groth-Pedersen, 2007; Boya, 2008; Roberg, 1998). Indeed, reducing ROS with either the compound having Formula 3 or the anti-oxidant vitamin C alleviated LMP in cold-exposed human iPSC-neurons (FIG. 2F). Taken together, impaired PQC components coupled with ROS overproduction by stressed mitochondria may form a vicious cycle, resulting in irreversible microtubule damage and aggregation in the cold. Remarkably, GS iPSC-neurons are immune to such adverse cellular responses, perhaps due to enhanced organelle membrane integrity allowed by a unique lipid redistribution in the cold (Azzam, 2000).

Figure 3A:
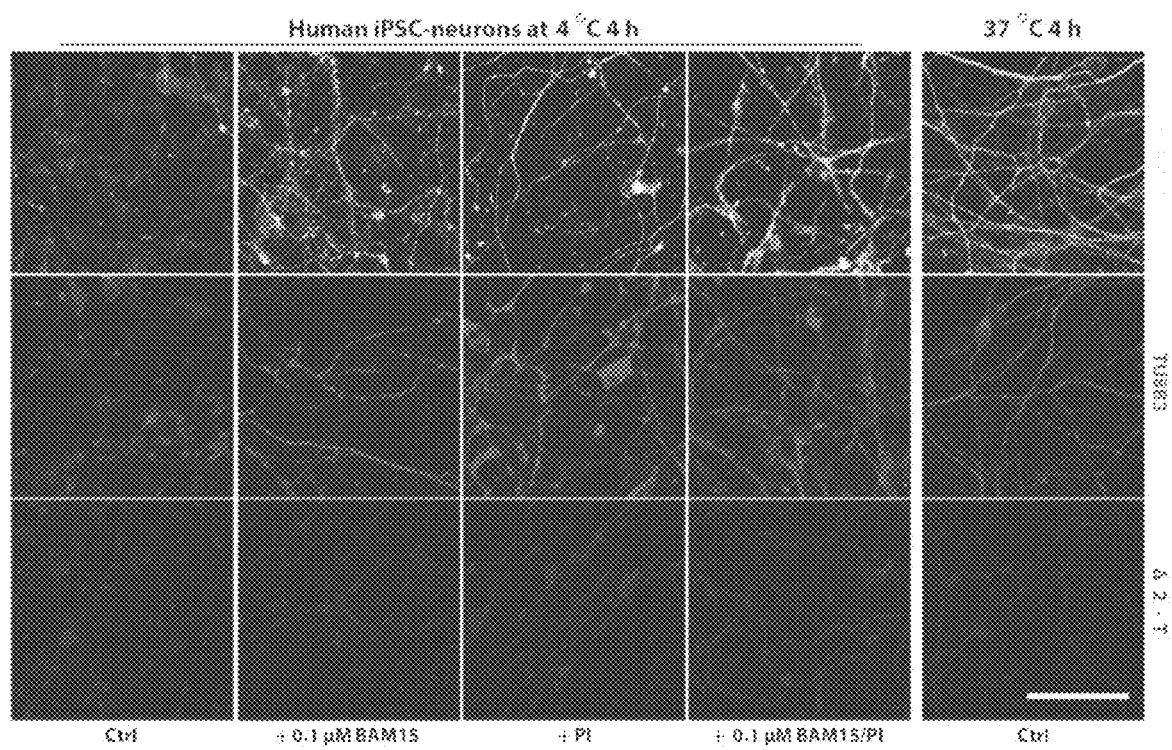
FIGS. 3A to 3D depict morphological protection of human iPSC-neurons by the compound having Formula 3/PI pretreatments against prolonged cold stress.
Figure 3B:
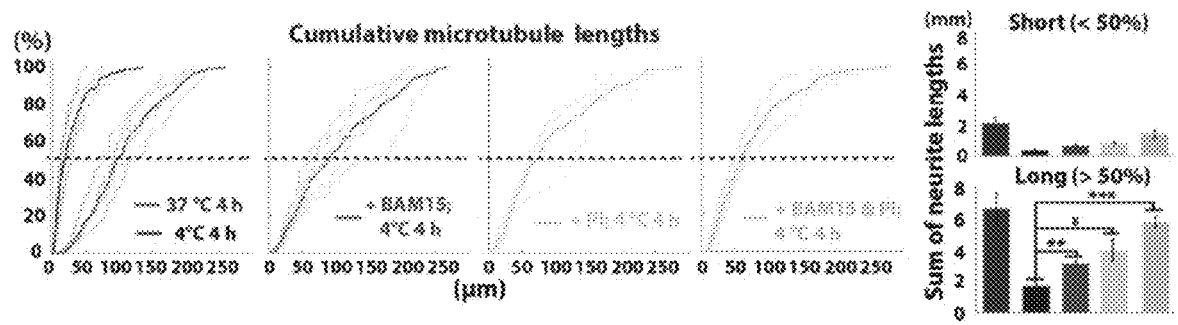
Figure 3C:
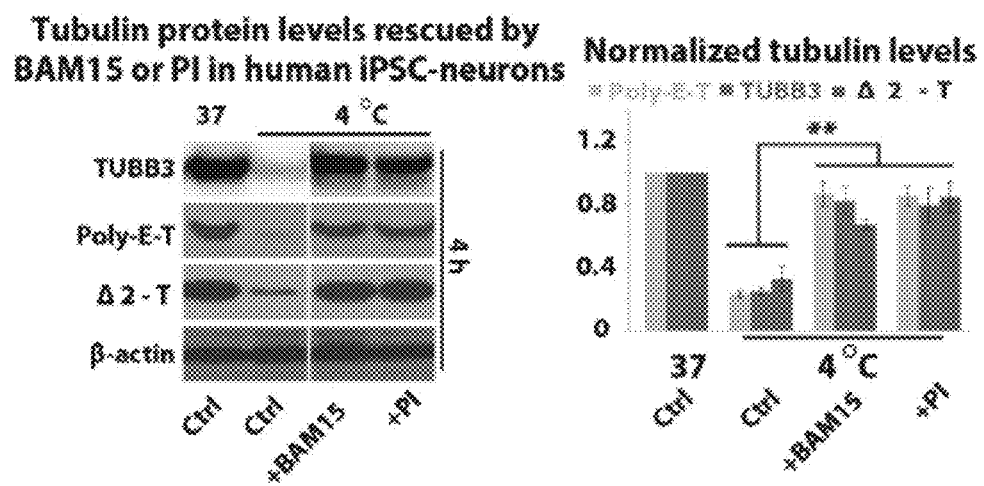
Figure 3D:
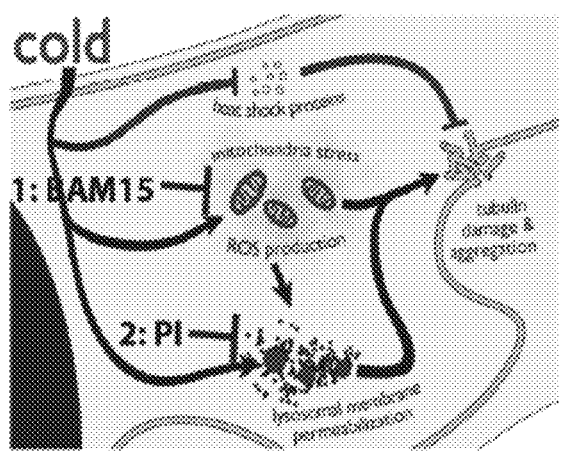

In view of the bioinformatics and experimental results, the inventors examined whether pharmacological intervention targeting the affected pathways could confer GS's microtubule cold resistance upon non-hibernating mammals. Indeed, human iPSC-neurons pretreated with the compound having Formula 3 or a protease inhibitor cocktail (PI) against leaked proteases from LMP largely stabilized microtubules following prolonged incubations at 4° C. (FIGS. 3A and 3B and FIGS. 10A and 10B). Furthermore, both treatments preserved tubulin proteins in cold-exposed human cells (FIG. 3C). Notably, PI did not alter $\Delta\psi_m$ hyperpolarization or ROS production (FIGS. 2A and 2B), consistent with LMP induction acting downstream of mitochondrial activities. Remarkably, the combination of the compound having Formula 3 and PI further preserved microtubules to near-normal levels (FIG. 3B), suggesting that in addition to triggering LMP, ROS may directly damage microtubules as demonstrated previously (FIG. 3D, Neely 1999; Landino 2004).

Figure 4B:
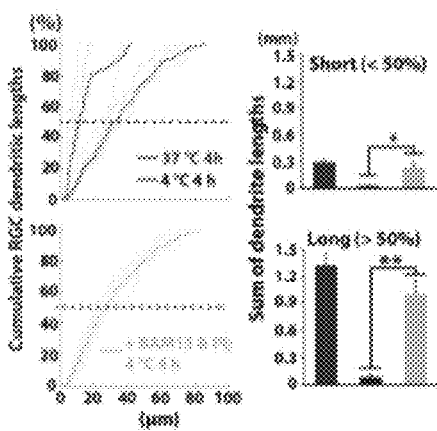
Figure 4C:
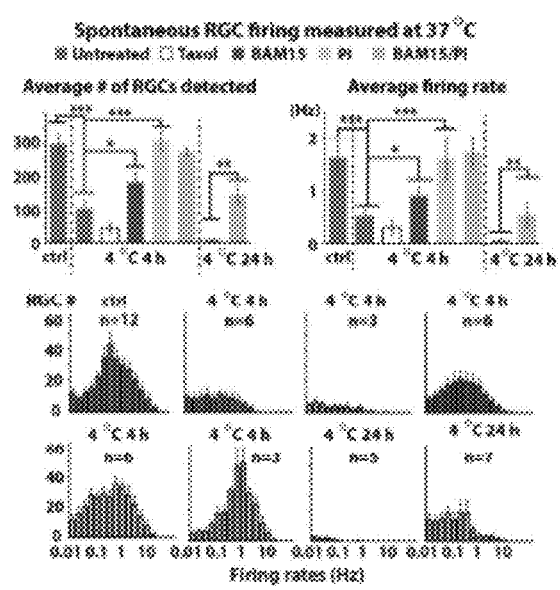

In view of these results, the inventors further tested whether the compound having Formula 3/PI could also protect neural tissues of a non-hibernator during extreme hypothermia. A rat retina preparation was used, which has an intact neural structure ex vivo and responds to light under healthy conditions. Like human iPSC-neurons, cold-exposed retinal ganglion cells (RGCs) in rat retina exhibited considerable microtubule disruption, losing most of their dendritic microtubules and forming numerous tubulin aggregates along their axons (FIGS. 4A and 4B). In contrast, retinal tissues from cold-exposed GS showed no changes in microtubule morphology (FIGS. 11A and 11B). Strikingly, pre-incubation of rat retinas with the compound having Formula 3 and PI greatly reduced these defects (FIGS. 4A and 4B).

Figure 4D:
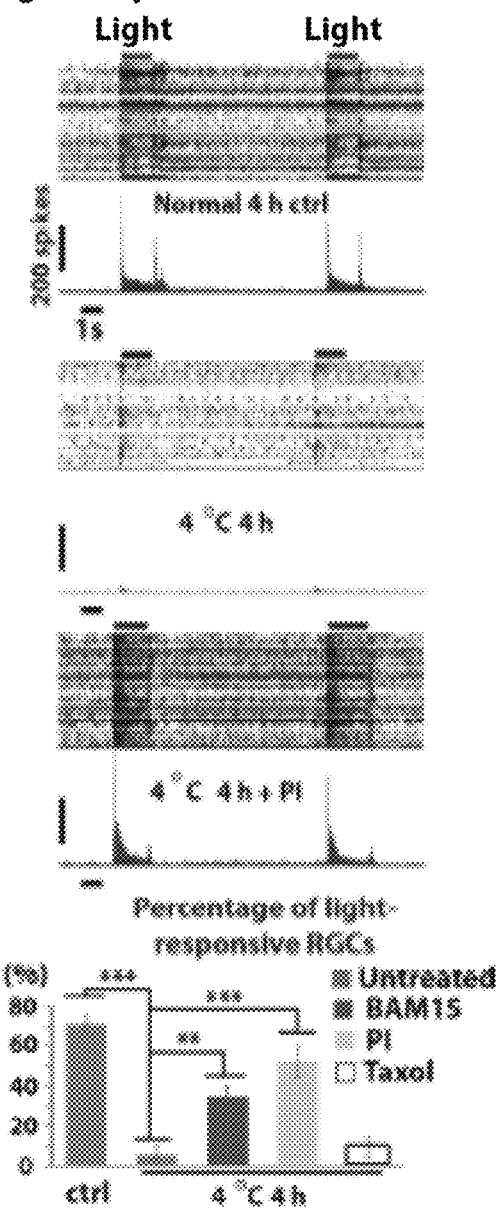

Multi-electrode array (MEA) recordings were then used to measure RGC activity. Incubation at 4° C. for 4 h largely silenced RGCs, whereas pre-treatment with the compound having Formula 3 and/or PI significantly preserved normal RGC firing rate distributions, but 10 µM Taxol (a microtubule stabilizer) did not preserve RGC activity (FIG. 4C) even though it preserved microtubules in cold (FIG. 6B). Importantly, approximately 70% of RGCs detected in normal retinas were light responsive (FIG. 4D), compared to only 5% in untreated retinas after 4° C. for 4 h; however, the compound having Formula 3 or PI (but not Taxol) pretreated retinas displayed 7-11 fold increases in light-responsiveness (FIG. 4D). Taken together, these results indicate that uncoupling mitochondria and/or inhibiting leaked lysosomal proteases not only increases microtubule stability, but in essence renders non-hibernating rat neural tissue cold tolerant.

Figure 4E:
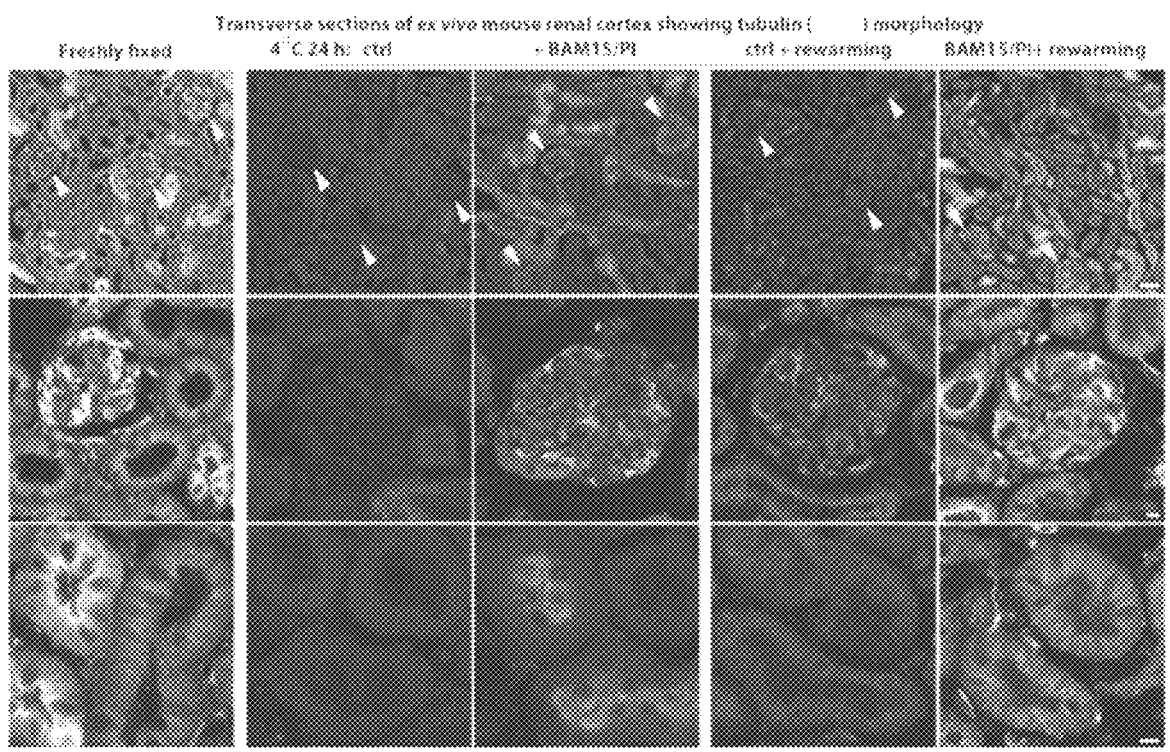

The inventors further tested whether such protection could be extended to non-neural tissues such as organs awaiting transplantation, commonly stored in conditions akin to hibernation. As reported previously (Breton, 1998; Mangino, 2008), it was found that mouse kidneys stored in University Wisconsin (UW) solution at 4° C. for 24 h exhibited microtubule damage with drastically reduced tubulin labeling (especially in glomeruli) and limited repolymerization after rewarming (FIG. 4E). Remarkably, adding the compound having Formula 3 and PI to UW solution significantly improved tubulin signals in the cold and bestowed prominent recovery of microtubule morphology after rewarming (FIG. 4E). In addition, the compound having Formula 3 and PI also greatly reduced protein/DNA damage caused by lipid peroxidation (FIG. 12), a known adverse effect of cold storage (Cotterill, 1989; Richer, 2000). These results indicate that the compound having Formula 3/PI treatment may confer cold protection to non-neural tissues and organs, prolonging their shelf-life for transplantation. This is promising for advancing applications of hypothermic therapy such as in cardiac arrest, ischemic stroke, or traumatic brain injury, where overcoming cold-induced cellular damage has been a major challenge (Marion, 1997). As demonstrated in this disclosure, GS iPSCs can be used to further elucidate cellular mechanisms of cold adaptation in hibernators to harness protective effects of hypothermia while mitigating harm.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A method for treating mammalian cells, tissues, or organs in need of protection from low-temperature injury, the method comprising:
   contacting the mammalian cells, tissues, or organs with a composition comprising:
   a compound of formula (I)

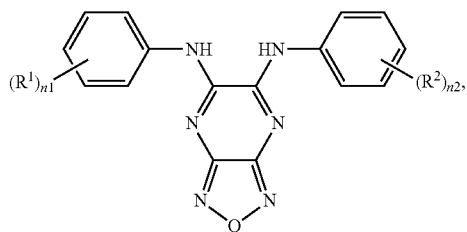
   Formula 1 a protease inhibitor selected from the group consisting of a cysteine protease inhibitor, an aspartic protease inhibitor, a serine protease inhibitor, and a leucine aminopeptidase inhibitor and
   a reducing agent; and
   exposing the mammalian cells, tissues, or organs to a temperature of from about 1-5° C.

2. The method according to claim 1, wherein the reducing agent is ascorbic acid.

3. The method according to claim 1, wherein the protease inhibitor is a combination of E-64, Pepstatin A, AEBSF, and Bestatin, and the reducing agent is ascorbic acid.

4. The method according to claim 1, further comprising admixing the composition with a cryopreservation agent to form a solution, wherein contacting the mammalian cells, tissues, or organs with the composition comprises contacting the mammalian cells, tissues, or organs with the solution.

5. The method according to claim 4, wherein the composition comprises the compound of Formula (I), E-64, Pepstatin A, AEBSF, Bestatin, and ascorbic acid, the solution having
   a concentration of the compound of Formula (I) from 0.05 to 0.2 μM;
   a concentration of E-64 from 3 to 5 μM;
   a concentration of Pepstatin A from 2 to 4 μM;
   a concentration of AEBSF from 100 to 200 μM;
   a concentration of Bestatin from 10 to 20 μM; and
   a concentration of ascorbic acid from 50 to 300 μM.

6. The method according to claim 1, wherein the mammalian cells, tissues, or organs are selected from the group consisting of neuronal cells, retinal cells, corneal cells, corneal tissue, a cornea, retina tissue, a retina, skin cells, skin tissue, skin, heart cells, heart tissue, a heart, lung cells, lung tissue, a lung, pancreal cells, pancreas tissue, a pancreas, kidney cells, kidney tissue, a kidney, liver cells, liver tissue, a liver, intestinal cells, intestinal tissue, intestine, stem cells, blood cells and blood.

7. The method according to claim 1, wherein the temperature is from 2° C. to 5° C.

8. The method according to claim 7 wherein the treatment has a duration from 4 to 72 hours.

9. The method according to claim 4 wherein the cryopreservation agent is a solution comprising hydroxyethyl starch 50.0 g/L; lactobionic acid (as Lactone) 35.83 g/L; potassium dihydrogen phosphate 3.4 g/L; magnesium sulfate heptahydrate 1.23 g/L; raffinose pentahydrate 17.83 g/L; adenosine 1.34 g/L; allopurinol 0.136 g/L; total glutathione 0.922 g/L; and potassium hydroxide 5.61 g/L, adjusted to pH 7.4.

10. The method according to claim 1 wherein the protease inhibitor consists essentially of the peptide Iva-Val-Val-Sta-Ala-Sta (Pepstatin A).

11. The method accordingly claim 9 wherein the hydroxyethyl starch comprises Pentafraction.

* * * * *